US008282935B2

(12) United States Patent
Cerundolo et al.

(10) Patent No.: US 8,282,935 B2
(45) Date of Patent: Oct. 9, 2012

(54) MATERIALS AND METHODS RELATING TO IMPROVED VACCINATION STRATEGIES

(75) Inventors: Vincenzo Cerundolo, Oxfordshire (GB); Michael J. Palmowski, Oxfordshire (GB); Edward Man-Lik Choi, Oxfordshire (GB)

(73) Assignee: ISIS Innovation Limited, Oxfordshire (GB)

( * ) Notice: Subject to any disclaimer, the term of this patent is extended or adjusted under 35 U.S.C. 154(b) by 153 days.

(21) Appl. No.: 12/017,421

(22) Filed: Jan. 22, 2008

(65) Prior Publication Data
US 2008/0260780 A1    Oct. 23, 2008

Related U.S. Application Data

(62) Division of application No. 10/485,074, filed as application No. PCT/GB02/03496 on Jul. 30, 2002, now abandoned.

(30) Foreign Application Priority Data

Jul. 30, 2001  (GB) .................................. 0118532.1

(51) Int. Cl.
A61K 35/00 (2006.01)
A61K 48/00 (2006.01)
C07H 21/04 (2006.01)
(52) U.S. Cl. .................. 424/199.1; 424/93.1; 424/93.2; 536/23.1; 536/23.4; 435/5; 435/6.1
(58) Field of Classification Search ........................ None
See application file for complete search history.

(56) References Cited

U.S. PATENT DOCUMENTS

| | | | |
|---|---|---|---|
| 4,053,582 A | 10/1977 | Stickl | |
| 4,748,019 A | 5/1988 | Lysons | |
| 5,110,587 A | 5/1992 | Paoletti et al. | |
| 5,185,146 A | 2/1993 | Altenburger | |
| 5,225,336 A | 7/1993 | Paoletti | |
| 5,453,364 A | 9/1995 | Paoletti | |
| 5,462,734 A | 10/1995 | Letchworth, III et al. | |
| 5,766,597 A | 6/1998 | Paoletti et al. | |
| 5,846,546 A | 12/1998 | Hurwitz et al. | |
| 6,103,244 A | 8/2000 | Dorner et al. | |
| 6,153,380 A * | 11/2000 | Nolan et al. | 435/6 |
| 6,355,252 B1 | 3/2002 | Smith et al. | |
| 6,663,871 B1 | 12/2003 | McMichael et al. | |
| 7,273,605 B2 | 9/2007 | Laidlaw et al. | |
| 7,384,643 B2 | 6/2008 | Smith et al. | |
| 7,407,661 B2 | 8/2008 | McMichael et al. | |
| 7,514,087 B2 | 4/2009 | McMichael et al. | |
| 2001/0036928 A1 | 11/2001 | Chamberlain et al. | |
| 2003/0138454 A1 | 7/2003 | Hill et al. | |
| 2004/0018177 A1 | 1/2004 | Hill et al. | |
| 2004/0131594 A1 | 7/2004 | McMichael et al. | |
| 2004/0142002 A1 | 7/2004 | Smith et al. | |
| 2004/0175365 A1 | 9/2004 | McMichael et al. | |
| 2004/0191272 A1 | 9/2004 | McMichael et al. | |
| 2004/0197349 A1 | 10/2004 | McMichael et al. | |
| 2004/0213799 A1 | 10/2004 | McMichael et al. | |
| 2005/0025747 A1 | 2/2005 | Laidlaw et al. | |
| 2005/0175627 A1 | 8/2005 | Schneider | |
| 2008/0267996 A1 | 10/2008 | Schneider et al. | |
| 2009/0191237 A1 | 7/2009 | McMichael et al. | |
| 2009/0324632 A1 | 12/2009 | McMichael et al. | |
| 2010/0119551 A1 | 5/2010 | McMichael et al. | |

FOREIGN PATENT DOCUMENTS

| | | |
|---|---|---|
| CN | 1 324 661 A | 12/2001 |
| EP | 0 638 316 A1 | 2/1995 |
| EP | 0 753 581 A1 | 1/1997 |
| EP | 0 517 292 B1 | 2/2000 |
| WO | WO 92/22641 A1 | 12/1992 |
| WO | WO 93/03145 | 2/1993 |
| WO | WO 96/03144 | 2/1996 |
| WO | WO 96/26271 A1 | 8/1996 |
| WO | WO 96/26962 | 9/1996 |
| WO | WO 97/39771 A1 | 10/1997 |
| WO | WO 98/04728 A1 | 2/1998 |
| WO | WO 98 56919 A | 12/1998 |
| WO | WO 99/21572 | 5/1999 |
| WO | WO 99/41383 A1 | 8/1999 |
| WO | WO 99/42597 | 8/1999 |
| WO | WO 00 40261 A | 7/2000 |
| WO | WO 01/02607 A1 | 1/2001 |
| WO | WO 01/14416 A2 | 3/2001 |
| WO | WO 01/19408 | 3/2001 |
| WO | WO 01 21201 A | 3/2001 |
| WO | WO 01/85932 A2 | 11/2001 |
| WO | WO 01/85932 A3 | 11/2001 |
| WO | WO 02/24224 A2 | 3/2002 |
| WO | WO 02/068654 A2 | 9/2002 |

(Continued)

OTHER PUBLICATIONS

Pittet et al. Expansion and Functional Maturation of Human tumor Antigen-specific CD8+ T Cells after Vaccination with Antigenic Peptide. Clinical Cancer Research. vol. 7. p. 796-803 (Suppl.).*
Storkus and Zarour. Melanoma antigens recognised by CD8+ and CD4+ T cells. Forum (Genova). Jul.-Sep. 2000;10(3):256-70. Review.*
Valmori et al. Enhanced generation of specific tumor-reactive CTL in vitro by selected Melan-A/MART-1 immunodominant peptide analogues. J Immunol. Feb. 15, 1998;160(4):1750-8.*
Van Baren et al. Genes Encoding Tumor-Specific Antigens Are Expressed in Human Myeloma Cells. Blood. 94:4, 1999, p. 1156-1164.*

(Continued)

Primary Examiner — Zachariah Lucas
Assistant Examiner — Michelle S Horning
(74) Attorney, Agent, or Firm — Hamilton, Brook, Smith & Reynolds, P.C.

(57) ABSTRACT

The invention provides novel vaccination strategies based on a prime-boost vaccination regiment. The inventors have determined improved ways of boosting an immune response in a patient previously primed or exposed to a plurality of epitopes. The improved method requires the epitopes in the boosting phase to be administered individually, i.e. held on separate peptide constructs.

8 Claims, 8 Drawing Sheets

FOREIGN PATENT DOCUMENTS

| | | |
|---|---|---|
| WO | WO 02/068654 A3 | 9/2002 |
| WO | WO 2005/026370 A2 | 3/2005 |
| WO | WO 2005/030964 A1 | 4/2005 |
| WO | WO 2006/061643 A1 | 6/2006 |
| WO | WO 2006/120474 A2 | 11/2006 |
| WO | WO 2006/125983 A1 | 11/2006 |

OTHER PUBLICATIONS

J. Schneider et al., "Enhanced Immunogenicity for CD8+ T Cell Induction and Complete Protective Efficacy of Malaria DNA Vaccination by Boosting With Modified Vaccinia Virus Ankara", Nature Medicine, Nature Publishing Co., vol. 4, No. 4, pp. 397-402, Apr. 1998.

J. Schneider et al., "Induction of CD8+ T Cell Using Heterologous Prime-Boost Immunisation Strategies", Immunological Reviews, Munksgaard, vol. 170, pp. 29-38, Aug. 1999.

T. Hanke et al., "Enhancement of MHC class I-restricted peptide-specific T cell induction by a DNA prime/MVA boost vaccination regime", Vaccine Butterworth Scientific, Guilford, GB, vol. 16, No. 5, pp. 439-445, Mar. 1998.

T. Hanke et al., "Effective indication of HIV-specific CTL by multi-epitope using gene gun in a combined vaccination regime", Vaccine, Butterworth Scientific, Guilford, GB, vol. 17, No. 6, pp. 589-596, Feb. 1999.

L. Mateo et al., "An HLA-A2 polyepitope vaccine for melanoma immunotherapy", Journal of Immunology (Balt., Md. 1950), vol. 163, No. 7, pp. 4058-4063, Oct. 1999.

Da Silva et al., (2001) J. of Cellular Physiology, 186:169-182.

Nilsson et al., (2001)Vaccine, 19: 3526-3536.

Wang et al., (1998) Infection and Immunity 66(9): 4193-4202.

Smith et al., (2001) Clinical Cancer Research 7: 4253-4261.

Couillin et al., (2001) Virology, 279: 136-141.

Rafati et al., (2001) Vaccine 19: 3369-3375.

Berglund et al., (1998) Nature Biotechnology. 16: 562-565.

Degano et al., (2000) Vaccine. 18: 623-632.

Mateo et al. (1999) J. of Immunology. 163: 4058-4063.

Firat et al., (1999) Eur. J. Immunol. 29: 3112-3121.

Karpoff et al., (2000) Cancer Gene Therapy. 7: 581-588.

Elliott et al., (1999) Vaccine; 17:2009-2019.

Carvalho, L.J.M., et al., "Malaria Vaccine: Candidate Antigens, Mechanisms, Constraints and Prospects," Scand. J. Immunol. 56:327-343 (2002).

Michael H. Newberg et al., "Importance of MHC Class I α2 and α3 Domains in the Recognition of Self and Non-Self MHC Molecules", The Journal of Immunology, 1996, 156: 2473-2480.

Michael H. Newberg et al., "Species Specificity in the Interaction of CD8 With the α3 Domain of MHC Class I Molecules", The Journal of Immunology, vol. 149, 136-142, No. 1, Jul. 1, 1992.

Manabu Tanabe at al., "Analysis of Xenoantigenicity of HLA Class I Molecules by a Complete Series of Human-Mouse Hybrid Genes", Transplantation, vol. 48, 135-140, No. 1, Jul. 1989.

Victor H. Engelhard et al., "Species-Specific Structural Differences in the α1 + α2 Domains Determine the Frequency of Murine Cytotoxic T Cell Precursors Stimulated by Human and Murine Class I Molecules", The Journal of Immunology, vol. 141, 1835-1839, No. 6, Sep. 15, 1988.

Helen McShane et al., "Enhanced Immunogenicity of CD4+ T-Ceil Responses and Protective Efficacy of a DNA-Modified Vaccinia Virus Ankara Prime-Boost Vaccination Regimen for Murine Tuberculosis", Infection and Immunity, Feb. 2001, vol. 69, No. 2, pp. 681-686.

Steffanie Sabbaj et al., "Cytokine profiles in seronegative volunteers immunized with a recombinant canarypox and gp120 prime-boost HIV-1 vaccine.", AIDS 2000, vol. 14, No. 10, pp. 1365-1374, 2000.

Tomas Hanke et al., "Effective Induction of Simian Immunodeficiency Virus-Specific Cytotoxic T Lymphocytes in Macaques by Using a Multiepitope Gene and DNA Prime-Modified Vaccinia Virus Ankara Boost Vaccination Regimen", Journal of Virology, Sep. 1999, pp. 7524-7532, vol. 73, No. 9.

T. Daemen et al., "Genetic immunization against cervical carcinoma: induction of cytotoxic T lymphocyte activity with a recombinant alphavirus vector expressing human papillomavirus type 16 E6 and E7", Gene Therapy (2000) 7, 1859-1866.

P. Colmenero et al., "Induction of P815 tumor immunity by recombinant Semliki Forest virus expressing the P1A gene", Gene Therapy (1999), 6, 1728-1733.

Javier Hernandez et al., "The Use of HLA A2.1/p53 Peptide Tetramers to Visualize the Impact of Self Tolerance on the TCR Repertoire", The Journal of Immunology, 2000, 164: 596-602.

Marco A. Purbhoo et al., "The Human CD8 Coreceptor Effects Cytotoxic T Cell Activation and Antigen Sensitivity Primarily by Mediating Complete Phosphorylation of the T Cell Receptor ζ Chain", The Journal of Biological Chemistry, vol. 279, No. 35, Aug. 31, 2001, pp. 32786-32792.

Ada, G., "Do Cytotoxic T Lymphocytes Clear Some HIV/SIV Infections?," J. Med. Primatol 25(3):158-162 (1996).

Afonso, C.L., et al., "The Genome of Fowlpox Virus," J. Virol. 74(8):3815-3831 (2000).

Ahlers, J.D., et al., "Cytokine-in-Adjuvant Steering of the Immune Response Phenotype to HIV-1 Vaccine Constructs," The Journal of Immunology, 158(8):3947-3958 (1997).

Aidoo, M., et al., "Recombinant Vaccinia Viruses for the Characterization of Plasmodium falciparum-specific Cytotoxic T Lymphocytes: Recognition of Processed Antigen Despite Limited Re-Stimulation Efficacy," Intl. Immunol. 9(5):731-737 (1997).

Aidoo, M., et al., "Identification of Conserved Antigenic Components for a Cytotoxic T Lymphocyte-Inducing Vaccine Against Malaria," Lancet 345(8956):1003-1007 (1995).

"AIDS Vaccines Trials Dangerous," Isis News No. 11/12, Ho, M., ed., Institute of Science in Society [online], Oct. 2001 [retrieved on Nov. 27, 2006]. Retrieved from the Internet URL:www.i-sis.org.uk/isisnews/i-sisnews11-19.php.

Allen, T.M. and Watkins, D.I., SIV and SHIV CTL Epitopes Identified in Macaques [online], Dec. 1998. Retrieved from the Internet <URL:http://hiv-web.lanl.gov/content/hiv-db/COMPENDIUM/1998/III/Allen98.pdf>.

Allsopp, C.E.M., et al., "Comparison of Numerous Delivery Systems for the Induction of Cytotoxic T Lymphocytes by Immunization," Eur. J. Immunol. 26:1951-1959 (1996).

Altman, J.D., and Feinberg, M.B., "HIV Escape: There and Back Again," Nature Med. 10(3): 229-230 (2004).

An, L.-L., and Whitton, J.L., "A Multivalent Minigene Vaccine, Containing B-Cell, Cytotoxic T-Lymphocyte, and $T_h$ Epitopes from Several Microbes, Induces Appropriate Responses In Vivo and Confers Protection against More than One Pathogen," Journal of Virology, 71(3): 2292-2302 (1997).

Anderson, et al., "Enhanced CD8 T Cell Response and Protective Efficacy Against Malaria Using Recombinant Fowlpox Virus in Heterologous Prime/Boost Immunisation Regimes," Abstract, Immunology 101(Supplement 1):32 (2000).

Anderson, R., "Treatment of Melanoma by Heterologous PrimeBoost Immunotherapy," Oxxon Therapeutics, TVLN Presentation given on Apr. 6, 2006 (17 pages).

Austyn, J.M. and Wood, K.J., "An Overview of Immune Responses," In Principles of Cellular and Molecular Immunology, (NY: Oxford University Press Inc.), pp. 42-44 (1993).

Bailey, J.R., et al., "Transmission of Human Immunodeficiency Virus Type 1 from a Patient Who Developed AIDS to an Elite Suppressor," Journal of Virology, 82(15):7395-7410 (2008).

Bakker, A.B.H., et al., "Identification of a Novel Peptide Derived from the Melanocyte-Specific GP100 Antigen as the Dominant Epitope Recognized by an HLA-A2.1-Restricted Anti-Melanoma CTL Line," Int. J. Cancer, 62: 97-102 (1995).

Bergmann, C.C., et al., "Flanking Residues Alter Antigenicity and Immunogenicity of Multi-Unit CTL Epitopes," The Journal of Immunology, 157(8): 3242-3249 (1996).

Berkner, K.L., "Development of Adenovirus Vectors for the Expression of Heterologous Genes," BioTechniques 6(7): 616-629 (1988).

Blanchard, T.J., et al., "Modified Vaccinia Virus Ankara Undergoes Limited Replication in Human Cells and Lacks Several Immunomodulatory Proteins: Implications for Use as a Human Vaccine," J. Gen. Virol. 79:1159-1167 (1998).

Blanchard, T., et al., "Future Vaccines for HIV," Lancet 348(9043):1741 (1996).

Borrow, P., et al., "Virus-Specific CD8+ Cytotoxic T-Lymphocyte Activity Associated with Control of Viremia in Primary Human Immunodeficiency Virus Type 1 Infection," *J. Virology* 68(9): 6103-6110 (1994).

Boulanger, D., et al., "Morphogenesis and Release of Fowlpox Virus," *J. Gen. Virol.* 81:675-687 (2000).

Boulanger, D., et al., "The 131-Amino-Acid Repeat Region of the Essential 39-Kilodalton Core Protein of Fowlpox Virus FP9, Equivilant to Vaccinia Virus A4L Protein, Is Nonessential and Highly Immunogenic," *J. Virol* 72(1):170-179 (1998).

Boursnell, M. E. G., et al., "A Fowlpox Virus Vaccine Vector with Insertion Sites in the Terminal Repeats: Demonstration of its Efficacy Using the Fusion Gene of Newcastle Disease Virus," *Vet. Microbiol.* 23:305-316 (1990).

Boursnell, M.E.G., et al., "Insertion of the Fusion Gene from Newcastle Disease Virus into a Non-essential Region in the Terminal Repeats of Fowlpox Virus and Demonstration of Protective Immunity Induced by the Recombinant," *J. Gen. Virol.* 71:621-628 (1990).

Boyle, D.B. and Heine, H. G., "Recombinant Fowlpox Virus Vaccines for Poultry," *Immunol. Cell Biol.* 71:391-397 (1993).

Boyle, D.B., et al., "Comparison of Field and Vaccine Strains of Australian Fowlpox Viruses," *Arch Viral* 142:737-748 (1997).

Brander, C. and Walker, B.D., The HLA Class I Restricted CTL Response in HIV-1 Infection: Systematic Identification of Optimal Epitopes. HIV Molecular Immunology Database [online], Feb. 2002 [retrieved on Oct. 19, 2006], Retrieved from the Internet <URL:http://www.hiv-web.lanl.gov>.

Brooks, J. V., et al., "Boosting Vaccine for Tuberculosis," *Infect. Immun.* 69(4):2714-2717 (2001).

Brossart, P., et al, "Virus-Mediated Delivery of Antigenic Epitopes into Dendritic Cells as Means to Induce CTL," *J. Immunol.* 158:3270-3276 (1997).

Buge, S.L., et al., "Factors Associated with Slow Disease Progression in Macaques Immunized with an Adenovirus-Simian Immunodeficiency Virus (SIV) Envelope Priming-gp120 Boosting Regimen and Challenged Vaginally with SIVmac251," *J. Virol.* 73(9):7430-7440 (1999).

Bukowski, J.F., et al., "Natural Killer Cell Depletion Enhances Virus Synthesis and Virus-Induced Hepatitis In Vivo," *The Journal of Immunology*, 131(3): 1531-1538 (1983).

Campbell, J.I.A., et al., "Tandem Repeated Sequences within the Terminal Region of the Fowlpox Virus Genome,"*J. Gen. Virol.* 70:145-154 (1989).

Carroll, M.W., et al., "Highly Attenuated Modified Vaccinia Virus Ankara (MVA) as an Effective Recombinant Vector: A Murine Tumor Model," *Vaccine* 15(4):387-394 (1997).

Carter, B.J., "Gene Therapy as Drug Development," *Mol. Therapy* 1:(3)211-212 (2000).

Casares, N., et al., "CD4$^+$/CD25$^+$ Regulatory Cells Inhibit Activation of Tumor-Primed CD4$^+$ T Cells with IFN-γ-Dependent Antiangiogenic Activity, as well as Long-Lasting Tumor Immunity Elicited by Peptide Vaccination," *The Journal of Immunology*, 171(11): 5931-5939 (2003).

Castelli, C., et al. "Mass Spectrometric Identification of a Naturally Processed Melanoma Peptide Recognized by CD8$^+$ Cytotoxic T Lymphocytes," *J. Exp. Med.* 181:363-368 (1995).

Chamberlain, R.S., et al., "Use of Recombinant Vaccination Vectors for the Generation of CTL Against a Model Tumor Antigen," *Proceedings of the Annual Meeting of the American Association for Cancer Research* (Washington, Apr. 20-24, 1996, 37, Abstract No. 3263).

Chamberlain, R.S., Poster Presentation presented at the Meeting of the American Association of Cancer Research, Apr. 20$^{th}$ through Apr. 24, 1996.

Chow, Y-H., et al., "Improvement of Hepatitis B Virus DNA Vaccines by Plasmids Coexpressing Hepatitis B Surface Antigen and Interleukin-2," *J. Virol.*, 71(1): 169-178 (1997).

Conry, R.M., et al., "Safety and Immunogenicity of a DNA Vaccine Encoding Carcinoembryonic Antigen and Hepatitis B Surface Antigen in Colorectal Carcinoma Patients," *Clin. Cancer Res.* 8:2782-2787 (2002).

Coupar, B.E.H., et al., "Restriction Endonuclease Mapping of the Fowlpox Virus Genome," *Virology* 179:159-167 (1990).

Cox, W.I., et al., Induction of Cytotoxic T Lymphocytes by Recombinant Canarypox (ALVAC) and Attenuated Vaccinia (NYVAC) Viruses Expressing the HIV-1 Envelope Glycoprotein, *Virology*, 195: 845-850 (1993).

Dale, C.J., et al., "Induction of HIV-1-Specific T-Helper Responses and Type 1 Cytokine Secretion Following Therapeutic Vaccination of Macaques with a Recombinant Fowlpoxvirus Co-expressing Interferon-Gamma," *J. Med. Primatol.* 29:240-247 (2000).

Davis, H.L., et al., "DNA-Mediated Immunization to Hepatitis B Surface Antigen: Longevity of Primary Response and Effect of Boost," *Vaccine* 14(9):910-915 (1996).

Denis, O., et al., "Vaccination with Plasmid DNA Encoding Mycobacterial Antigen 85A Stimulates a CD4$^+$ and CD8$^+$ T-Cell Epitopic Repertoire Broader than that Stimulated by *Mycobacterium tuberculosis* H37Rv Infection," *Infect. Immun.* 66(4):1527-1533 (1998).

Desrosiers, R.C., "Prospects for an AIDS Vaccine," *Nature Med.* 10(3):221-223 (2004).

Doolan, D.L., et al., "Circumventing Genetic Restriction of Protection against Malaria with Multigene DNA Immunization: CD8$^+$ T Cell-, Interferon γ-, and Nitric Oxide-Dependent Immunity," *J. Exp. Med.* 183(4): 1739-1746 (1996).

Doolan, D.L. and Hoffman, S.L., "The Complexity of Protective Immunity Against Liver-Stage Malaria," *J. Immunol.* 165(3):1453-1462 (2000).

"Dose-Ranging Study to Evaluate the Safety & Immunogenicity of a HIV Vaccine 732461 in Healthy HIV Seronegative Volunteers," [online], Feb. 2007 [retrieved on Mar. 7, 2007], Retrieved from the Internet <URL:http://www.clinicaltrials.gov>.

Drexler, I., et al., "Highly Attenuated Modified Vaccinia Virus Ankara Replicates in Baby Hamster Kidney Cells, a Potential Host for Virus Propagation, but not in Various Human Transformed and Primary Cells," *J. Gen. Virol.* 79:347-352 (1998).

Egan, M.A., et al., "Induction of Human Immunodeficiency Virus Type 1 (HIV-1)-Specific Cytolytic T Lymphocyte Responses in Seronegative Adults by a Nonreplicating, Host-Range-Restricted Canarypox Vector (ALVAC) Carrying the HIV-1$_{MN}$env Gene," *J. Infectious Diseases* 171:1623-1627 (1995).

Egan, M.A., et al., "Use of Major Histocompatibility Complex Class I/Peptide/β2M Tetramers To Quantitate CD8$^+$ Cytotoxic T Lymphocytes Specific for Dominant and Nondominant Viral Epitopes in Simian-Human Immunodeficiency Virus-Infected Rhesus Monkeys," *Journal of Virology*, 73(7): 5466-5472 (1999).

Eisenlohr, L.C., et al., "Flanking Sequences Influence the Presentation of an Endogenously Sythesized Peptide to Cytotoxic T Lymphocytes," *The Journal of Experimental Medicine*, 175: 481-487 (1992).

E-mail dated Jan. 5, 2006 from American Society for Microbiology re: Date of Disclosure of Buge's Document.

'Epitope Maps', HIV Molecular Immunology Database, [online] [Retrieved from the Internet on Jun. 23, 2003]. <URL:http://hiv-web.lanl.gov/content/immunology/maps/maps.html.>.

Fang, Z.-Y., et al., "Expression of Vaccina E3L and K3L Genes by a Novel Recombinant Canarypox HIV Vaccine Vector Enhances HIV-1 Pseudovirion Production and Inhibits Apoptosis in Human Cells," *Virology* 291:272-284 (2001).

Feng, C.G., et al., "Induction of CD8$^+$ T-lymphocyte Responses to a Secreted Antigen of *Mycobacterium Tuberculosis* by an Attenuated Vaccinia Virus," *Immunol. Cell Biol.* 79:569-575 (2001).

Franchini, G., et al., "Highly Attenuated HIV Type 2 Recombinant Poxviruses, but not HIV-2 Recombinant *Salmonella* Vaccines, Induce Long-lasting Protection in Rhesus Macaques," *AIDS Res. Hum. Retroviruses* 11(8):909-920 (1995).

Friedrich, T.C., et al., "Reversion of CTL Escape—Variant Immunodeficiency Viruses in vivo," *Nature Med.* 10(3):275-281 (2004).

Fuller, D.H., et al., "Enhancement of Immunodeficiency Virus-Specific Immune Responses in DNA-immunized Rhesus Macaques," *Vaccine* 15(8):924-926 (1997).

Fuller, D.H., et al., "Gene Gun-Based Nucleic Acid Immunization Alone or in Combination with Recombinant Vaccinia Vectors Suppresses Virus Burden in Rhesus Macaques Challenged with a Heterologous SIV," *Immunol. Cell Biol.* 75(4):389-396 (1997).

Gallimore, A., et al., "Early Suppression of SIV Replication by CD8+ nef-specific Cytotoxic T Cells in Vaccinated Macaques," Nature Med. 1(11):1167-1173 (1995).

Gherardi, M.M., et al., "Prime Boost Immunization Schedules Based on Influenza Virus and Vaccinia Virus Vectors Potentiate Cellular Immune Responses Against Human Immunodeficiency Virus Env Protein Systemically and in the Genitorectal Draining Lymph Nodes," The Journal of Virology, 77(12): 7048-7057 (2003).

Gilbert, S.C., et al., "A Protein Particle Vaccine Containing Multiple Malaria Epitopes," Nature Biotechnol. 15:1280-1284 (Nov. 1997).

Gilbert, S.C., et al., "DNA Immunisation of Mice with Plasmodium berghei Antigene: Use of Whole Antigens or Multi-epitope Strings, Boosting with Vaccinia and Protection Against Challenge," Immunol. Lett., 56/1-3: 28 (1997) (From Malaria and Other Tropical Diseases Abstracts, 1997, Abstract No. 0.4.05.7).

Gönczöl, E., et al., "Preclinical Evaluation of an ALVAC (canarypox)-human Cytomegalovirus Glycoprotein B Vaccine Candidate," Vaccine, 13(12): 1080-1085 (1995).

Greenspan, N.S. and DiCera, E., "Defining Epitopes: It's not as Easy as it Seems," Nature Biotechnol. 17:936-937 (1999).

Grosenbach, D.W., et al., "Synergy of Vaccine Strategies to Amplify Antigen-specific Immune Responses and Antitumor Effects," Cancer Res. 61:4497-4505 (2001).

Haigwood, N.L., "Predictive Value of Primate Models for AIDS," AIDS Reviews 6:187-198 (2004).

Hanke, T., et al., "DNA and MVA-based Multi-CTL Epitope Vaccines for HIV and Plasmodium falciparum: Immunogenicity in Mice and Macaques," Immunol. Lett., 56/1-3: 291 (1997) (From Poster Presentations Abstracts, 1997, Abstract No. P.4.01.22).

Hanke, T., et al., "DNA Multi-CTL Epitope Vaccines for HIV and Plasmodium falciparum: Immunogenicity in Mice," Vaccine 16(4):426-435 (1998).

Hanke, T., et al., "Immunogenicities of Intravenous and Intramuscular Administrations of Modified Vaccinia Virus Ankara-based Multi-CTL Epitope Vaccine for Human Immunodeficiency Virus Type 1 in Mice," J. Gen. Virol. 79:83-90 (1998).

Hertig, C., et al., "Field and Vaccine Strains of Fowlpox Virus Carry Integrated Sequences from the Avian Retrovirus, Reticuloendotheliosis Virus," Virology 235:367-376 (1997).

Hill, A.V.S., et al., "Common West African HLA Antigens are Associated with Protection from Severe Malaria," Nature 352(6336):595-600 (1991).

Hill, A.V.S., et al., "DNA-Based Vaccines for Malaria: a Heterologous Prime-Boost Immunisation Strategy," Dev. Biol. 104:171-179 (2000).

Hirsch, V.M., et al., "Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara," J. Virol. 70(6):3741-3752 (1996).

HIV CTL Epitopes Table 2: p. 24. [online], Dec. 1996. Retrieved from the Internet <URL:http://hiv-web.lanl.gov/content/immunology/pdf/1996/CTL/TABLES/p24.pdf>.

HIV CTL Epitopes Table 3: p. 24 [online], Dec. 1999. Retrieved from the Internet <URL:http://hiv-web.lanl.gov/content/immunology/pdf/1999/1/tables/p24.pdf>.

HIV CTL Epitopes Table 4: Pol [online], Dec. 1997. Retrieved from the Internet <URL:http://hiv-web.lanl.gov/content/hiv-db/immunology/PDF/1997/CTL/tables/pol.pdf>.

HIV CTL Epitopes Table 6: gp120. [online], Dec. 1996. Retrieved from the Internet <URL:http://hiv-web.lanl.gov/content/immunology/pdf/1996/CTL/TABLES/gp120.pdf>.

HIV CTL Epitopes Table 7: gp41. [online], Dec. 1996. Retrieved from the Internet <URL:http://hiv-web.lanl.gov/content/immunology/pdf/1996/CTL/TABLES/gp41.pdf>.

HIV CTL Epitopes Table 8: Net. [online], Dec. 1996. Retrieved from the Internet <URL:http://hiv-web.lanl.gov/content/immunology/pdf/1996/CTL/TABLES/nef. pdf>.

Hodge, J.W., et al., "Diversified Prime and Boost Protocols Using Recombinant Vaccinia Virus and Recombinant Non-Replicating Avian Pox Virus to Enhance T-Cell Immunity and Antitumor Responses," Vaccine 15(6/7):759-768 (Apr./May 1997).

Holder, A., et al., "Falciparum Malaria MSP1 Workshop: Progress toward MSP1 Vaccine Development and Testing," Malaria Vaccine Initiative at PATH: 1-30 (2000).

Hu, S.-L., "Non-Human Primate Models for AIDS Vaccine Research," Curr. Drug Targets Infect. Disord., 5(2):193-201 (2005).

Hu, S.-L., et al., "Protection of Macaques Against SIV Infection by Subunit Vaccines of SIV Envelope Glycoprotein gp160," Science, 255: 456-459 (1992).

Hunter, C.A., "How are NK Cell Responses Regulated During Infection?," Experimental Parasitology, 84: 444-448 (1996).

Hutchings, C.L., et al., "Novel Protein and Poxvirus-Based Vaccine Combinations for Simultaneous Induction of Humoral and Cell-Mediated Immunity," J. Immunol., 175: 599-606 (2005).

Huygen, K., et al., "Immunogenicity and Protective Efficacy of a Tuberculosis DNA Vaccine," Nature Med. 2(8): 893-898 (1996).

Irvine, K., et al., "Comparison of a CEA-Recombinant Vaccinia Virus, Purified CEA, and an Anti-Idiotype Antibody Bearing the Image of a CEA Epitope in the Treatment and Prevention of CEA-Expressing Tumors," Vaccine Res. 2(2):79-94 (1993).

Irvine, K.R., et al., "Enhancing Efficacy of Recombinant Anticancer Vaccines with Prime/Boost Regiments that use two Different Vectors," J. Natl. Cancer Inst. 89(21): 1595-1601 (1997).

Irvine, K.R., et al., "Route of Immunization and the Therapeutic Impact of Recombinant Anticancer Vaccines," J. Natl. Cancer Inst. 89(5):390-392 (1997).

Janeway, C.A., et al., "General Properties of Armed Effector T Cells," In Immuno Biology, (NY: Garland Publishing a member of the Taylor & Francis Group) p. 319 (2001).

Johnson, R.P., et al., "Induction of a Major Histocompatibility Complex Class I-Restricted Cytotoxic T-Lymphocyte Response to a Highly Conserved Region of Human Immunodeficiency Virus Type 1 (HIV-1) gp120 in Seronegative Humans Immunized with a Candidate HIV-1 Vaccine,"J. Virol. 68(5):3145-3153 (1994).

Kazanji, M., et al. "Expression and Immunogenicity in Rats of Recombinant Adenovirus 5 DNA Plasmids and Vaccinia Virus Containing the HTLV-I inv Gene," Int. J. Cancer 71:300-307 (1997).

Kent, S.J., et al., "A Recombinant Avipoxvirus HIV-1 Vaccine Expressing Interferon-gamma is Safe and Immunogenic in Macaques," Vaccine 18:2250-2256 (2000).

Kent, S.J., et al., "Analysis of Cytotoxic T Lymphocyte Responses to SIV Proteins in SIV-Infected Macaques Using Antigen-Specific Stimulation with Recombinant Vaccinia and Fowl Poxviruses," AIDS Res. Hum. Retroviruses 10(5):551-560 (1994).

Kent, S.J., et al., "Enhanced T-Cell Immunogenicity and Protective Efficacy of a Human Immunodeficiency Virus Type 1 Vaccine Regimen Consisting of Consecutive Priming with DNA and Boosting with Recombinant Fowlpox Virus," J. Virol. 72(12):10180-10188 (1998).

Kmieciak, D., et al., "Enhancement of Cellular and Humoral Immune Responses to Human Immunodeficiency Virus Type 1 Gag and Pol by a G/P-92 Fusion Protein Expressing Highly Immunogenic Gag p17/p24 and Pol p51 Antigens," J. Hum. Virol. 4(6):306-316(2001).

Koziel, M.J., "The Role of Immune Responses in the Pathogenesis of Hepatitis C Virus Infection," J. Viral Hepatitus 4(2):31-41 (1997).

Koziel, M.J. and Walker, B.D., "Characteristics of the Intrahepatic Cytotoxic T Lymphocyte Response in Chronic Hepatitis C Virus Infection," Spriner Seminars in Immunopathology, 19(1):69-83 (1997).

Konishi, E., et al., "Induction of Japanese Encephalitis Virus-specific Cytotoxic T Lymphocytes in Humans by Poxvirus-based JE Vaccine Candidates," Vaccine, 16(8): 842-849 (1998).

Konishi, E., et al., "Poxvirus-Based Japanese Encephalitis Vaccine Candidates Induce JE Virus-Specific CD8+ Cytotoxic T Lymphocytes in Mice," Virology, 227: 353-360 (1997).

Kuby, J.,"Cell-Mediated and Humoral Effector Responses," in Immunology, (NY: W. H. Freeman and Company) pp. 379-412 (1997).

Laidlaw, S.M. and Skinner, M.A., "Comparison of the Genome Sequence of FP9, an attenuated, tissue culture-adapted European strain of Fowlpox virus, with those of virulent American and European viruses," J. Gen. Virol. 85:305-322 (2004).

Laidlaw, S.M., et al., "Fowlpox Virus Encodes Nonessential Homologs of Cellular Alpha-SNAP, PC-1, and an Orphan Human Homolog of a Secreted Nematode Protein," *J. Virol.* 72(8):6742-6751 (1998).

Lalvani, A., et al., "An HLA-Based Approach to the Design of a CTL-Inducing Vaccine Against *Plasmodium falciparum*," *Res. Immunology* 145(6):461-468 (1994).

Lanar, D.E., et al., "Attenuated Vaccinia Virus-Circumsporozoite Protein Recombinants Confer Protection against Rodent Malaria," *Infec. Immun.* 64(5):1666-1671 (1996).

Layton, G.T., et al., "Induction of Single and Dual Cytotoxic T-Lymphocyte Responses to Viral Proteins in Mice Using Recombinant Hybrid Ty-Virus-Like Particles," *Immunology* 87(2):171-178 (1996).

Leong, K.H., et al., "Selective Induction of Immune Responses by Cytokines Coexpressed in Recombinant Fowlpox Virus," *J. Virol.* 68(12):8125-8130 (1994).

Leong, K.H., et al., "Generation of Enhanced Immune Responses by Consecutive Immunization with DNA and Recombinant Fowl Pox Vectors," *Vaccines* 95:327-331 (1995).

Leslie, A.J., et al., "HIV Evolution: CTL Escape Mutation and Reversion After Transmission," *Nature Med.* 10(3):282-289 (2004).

Letvin, n. L., "Progress Toward an HIV Vaccine," *Annu. Rev. Med.* 56:213-223 (2005).

Li, S., et al., "Priming with Recombinant Influenza Virus Followed by Administration of Recombinant Vaccinia Virus Induces CD8+ T-Cell-Mediated Protective Immunity against Malaria," *Proc. Natl. Acad. Sci. USA* 90(11):5214-5218 (1993).

Limbach, K.J. and Paoletti, E., "Non-Replicating Expression Vectors: Application in Vaccine Development and Gene Therapy," *Epidemiol. Infect.* 116:241-256 (1996).

Lindsey, K.R., et al., "Evaluation of Prime/Boost Regimens Using Recombinant Poxvirus/Tyrosinase Vaccines for the Treatment of Patients with Metastatic Melanoma," *Clin. Cancer Res.*, 12(8): 2526-2537 (2006).

Linnemeyer, P.A., "The Immune System—An Overview," [online] Nov. 1993 [retrieved on Apr. 12, 2006]. Retrieved from the Internet <URL:http://www.thebody.com/step/immune.html>.

Mahnel, et al., "Experiences with Immunization Against Orthopox Viruses of Humans and Animals Using Vaccine Strain MVA," *Berliner Und Munchener Tierarztliche Wochenschrift* 107(8):253-256 (1994) Abstract Only.

Malcherek, G., et al., "Supermotifs Enable Natural Invariant Chain-derived Peptides to Interact with Many Major Histocompatibility Complex-Class II Molecules," *J. Exp. Med.*, 181: 527-536 (1995).

Marshall, J.L., et al., "Phase I Study in Advanced Cancer Patients of a Diversified Prime-and-Boost Vaccination Protocol using Recombinant Vaccinia Virus and Recombinant Nonreplicating Avipox Virus to Elicit Anti-Carcinoembryonic Antigen Immune Responses," *J. Clin. Oncol.*, 18(23): 3964-3973 (2000).

Martin, R.M. and Lew, A.M., "Is IgG2a a Good Th1 Marker in Mice?" *Immunology Today*, 19:49 (1998).

Matano, T., et al., "Administration of an Anti-CD8 Monoclonal Antibody Interferes with the Clearance of Chimeric Simian/Human Immunodeficiency Virus during Primary Infections of Rhesus Macaques," *J. Virology* 72(1): 164-169 (1998).

Mayr, A. and Malicki, K., "Attenuierung von virulentem Hühnerpockenvirus in Zellkulturen und Eigenschaften des attenuierten Virus," *Zbl. Vet. Med. B* B13:1-13 (1966). (English Abstract attached.).

Meyer, H., et al., "Mapping of Deletions in the Genome of the Highly Attenuated Vaccinia Virus MVA and their Influence on Virulence," *J. Gen. Virol.* 72:1031-1038 (1991).

Moorthy, V.S., et al., "Safety of DNA and Modified Vaccina Virus Ankara Vaccines Against Liver-Stage *P. falciparum* Malaria in Non-Immune Volunteers," *Vaccine* 21:1995-2002 (2003).

Moorthy, V. and Hill, A.V.S., "Malaria Vaccines," *Br. Med. Bull.* 62:59-72 (2002).

Moreno, A., et al., "Cytotoxic CD4+ T Cells From a Sporozoite-Immunized Volunteer Recognize the *Plamodium falciparum* CS Protein," *Int. Immunol.* 3(10):997-1003 (1991).

Moss, B., "Genetically Engineered Poxviruses for Recombinant Gene Expression, Vaccination, and Safety," *Proc. Natl. Acad. Sci. USA* 93:11341-11348 (1996).

Moss, B., et al., "Host Range Restricted, Non-Replicating Vaccinia Virus Vectors as Vaccine Candidates." In *Novel Strategies in Design and Production of Vaccines*, S.Cohen et al., eds. (NY:Plenum Press), pp. 7-13 (1996).

Müllner, H.-M., et al., "Thrombospondin Related Anonymous Protein (TRAP) of *Plasmodium falciparum* Binds Specifically to Sulfated Glycoconjugates and to HepG2 Hepatoma Cells Suggesting a Role for this Molecule in Sporozoite Invasion of Hepatocytes," *EMBO J.* 12(7):2881-2889 (1993).

Müller, H.M., et al., "Thrombospondin Related Anonymous Protein (TRAP) of *Plasmodium Falciparum* in Parasite-Host Cell Interactions," *Parassitologia* 35(*Suppl.*): 69-72 (1993).

Murata, K., et al., "Characterization of in Vivo Primary and Secondary CD8+ T Cell Responses Induced by Recombinant Influenza and Vaccinia Viruses," *Cell. Immunol.* 173(1):96-107 (1996).

Nardin, E.H. and Nussenzweig, R.S., "T Cell Responses to Pre-Erythrocytic Stages of Malaria: Role in Protection and Vaccine Development Against Pre-Erythrocytic Stages," *Annu. Rev. Immunol.* 11:687-727 (1993).

Narvaiza, I., et al., Intratumoral Coinjection of Two Adenoviruses, One Encoding the Chemokine IFN-γ-Inducible Protein-10 and Another Encoding IL-12, Results in Marked Antitumoral Synergy, *The Journal of Immunology*, 164(6): 3112-3122 (2000).

Natuk, R.J., et al., "Immunogenicity of Recombinant Human Adenovirus-Human Immunodeficiency Virus Vaccines in Chimpanzees," *Aids Res. Hum. Retroviruses* (9):395-404 (1993).

NCBI Accession No. AF198100, "Fowlpox virus, complete genome," [online], Mar. 2000. [retrieved on Sep. 14, 2006] Retrieved from the Internet <URL:http://www.ncbi.nlm.nih.gov/entrez/viewer.fcgi?db=nucleotide&val=7271507>.

Niewiesk, S., et al., "Measles Virus-Induced Immune Suppression in the Cotton Rat (*Sigmodon hispidus*) Model Depends on Viral Glycoproteins," *J. Virol.* 71(10):7214-7219 (1997).

Notice of Opposition to a European Patent. Patent No. EP 1 214 416. Opponent: Transgene S.A. (English translation attached.) [Date signed by Opponent: Feb. 3, 2006; Date filed in EPO: Feb. 6, 2006].

Notice of Opposition to a European Patent. Patent No. EP 1 214 416 B1. Opponent: Merck & Co., Inc. [Date signed by Opponent: Feb. 9, 2006; Date filed in EPO: Feb. 13, 2006].

Notice of Opposition to a European Patent. Patent No. EP 1 214 416 B1. Opponent: Crucell Holland B.V. [Date signed by Opponent: Feb. 6, 2006; Date filed in EPO: Feb. 13, 2006].

Ohminami, H., et al., "HLA Class I-Restricted Lysis of Leukemia Cells by a CD8+ Cytotoxic T-Lymphocyte Clone Specific for WT1 Peptide," *Blood* 95(1):286-293 (2000).

Ojcius, D. M., et al., "Is Antigen Processing Guided by Major Histocompatibility Complex Molecules?," *FASEB J.*, 8: 974-978 (1994).

Okuda, K., et al., "Induction of Potent Humoral and Cell-Mediated Immune Responses Following Direct Injection of DNA Encoding the HIV Type 1 env and rev Gene Products," Aids Research and Human Retroviruses, 11(8): 933-943 (1995).

Paoletti, E., "Applications of Pox Virus Vectors to Vaccination: An Update," *Proc. Natl. Acad. Sci. USA* 93:11349-11353 (1996).

Pialoux, G., et al., "A Prime-Boost Approach to HIV Preventive Vaccine Using a Recombinant Canarypox Virus Expressing Glycoprotein 160 (MN) Followed by a Recombinant Glycoprotein 160 (MN/LAI)," *AIDS Res. Hum. Retroviruses*, 11(3):373-381 (1995).

Picard, O., et al., "Complication of Intramuscular/Subcutaneous Immune Therapy in Severely Immune-compromised Individuals," *J. Acquir. Immune Defic. Syndr.*, 4(6):641-643 (1991).

Plebanski, M., et al., "Protection From *Plasmodium berghei* Infection by Priming and Boosting T Cells to a Single Class I-Restricted Epitope with Recombinant Carriers Suitable for Human Use," *Eur. J. Immunol.*, 28(12):4345-4355 (1998).

Plebanski, M., et al., "Protection from *Plasmodium berghei* Infection by Priming to a Single CTL epitope with Vaccine Carriers that do not Require Adjuvants," *Immunol. Lett.*, 56/1-3: 425 (1997) (From *Poster Presentations Abstracts*, 1997, Abstract No. P.4.05.08).

Pollitt, E., et al., "Nucleotide Sequence of the 4.3 kbp BamHI-N Fragment of Fowlpox Virus FP9," *Virus Genes* 17(1):5-9 (1998).

Puig, M., et al., "CD4+ Immune Escape and Subsequent T-Cell Failure Following Chimpanzee Immunization Against Hepatitis C Virus," *Hepatology*, 44:736-745 (2006).

Puls, R.L. and Emery, S., "Therapeutic Vaccination against HIV: Current Progress and Future Possibilities," *Clin. Sci.*, 110(I):59-71 (2006).

Qingzhong, Y., et al., "Protection Against Turkey Rhinotracheitis Pneumovirus (TRTV) Induced by a Fowlpox Virus Recombinant Expressing the TRTV Fusion Glycoprotein (F)," *Vaccine* 12(6):569-573 (1994).

Ramarathinam, L., et al.,"Multiple Lineages of Tumors Express a Common Tumor Antigen, P1A, but they are not Cross-Protected," *J. Immunol*. 155:5323-5329 (1995).

Ramirez, J.C., et al., "Biology of Attenuated Modified Vaccinia Virus Ankara Recombinant Vector in Mice: Virus Fate and Activation of B- and T-Cell Immune Responses in Comparison with the Western Reserve Strain and Advantages as a Vaccine," *Journal of Virology*, 74(2): 923-933 (2000).

Reece, W.H.H., et al., "A DNA/MVA Prime-Boost Vaccination Regime Induces Strong Immune Responses and Partial Protection Against *Plasmodium falciparum* in Humans," *Poster at the British Society for Immunology* (Dec. 2001).

Reusser, P., et al., "Cytomegalovirus-Specific T-Cell Immunity in Recipients of Autologous Peripheral Blood Stem Cell or Bone Marrow Transplants," *Blood*, 89(10): 3873-3879 (1997).

Richmond, J.F.L., et al., "Screening of HIV-1 Env Glycoproteins for the Ability to Raise Neutralizing Antibody Using DNA Immunization and Recombinant Vaccinia Virus Boosting," *Virology* 230:265-274 (1997).

Riddell, S.R. and Greenberg, P.D., "Principles for Adoptive T Cell Therapy of Human Viral Diseases," *Annu. Rev. Immunol*. 13: 545-586 (1995).

Riddell, S.R., et al. "Restoration of Viral Immunity in Immunodeficient Humans by the Adoptive Transfer of T Cell Clones," *Science* 257 (1992).

Rimoldi, D., et al., "Efficient Simulataneous Presentation of NY-ESO-1/LAGE-1 Primary and Nonprimary Open Reading Frame-Derived CTL Epitopes in Melanoma," *J. Immunol.*, 165:7253-7261 (2000).

Robert-Guroff, M., et al., "Vaccine Protection Against a Heterologous, Non-Syncytium-Inducing, Primary Human Immunodeficiency Virus," *J. Virol*. 72(12):10275-10280 (1998).

Robinson, H. L., et al., "Neutralizing Antibody-independent Containment of Immunodeficiency Virus Challenges by DNA Priming and Recombinant Pox Virus Booster Immunizations," *Nature Med*. 5(5):526-534 (1999).

Rodriguez, D., et al., "Regulated Expression of Nuclear Genes by T3 RNA Polymerase and *lac* Repressor, Using Recombinant Vaccinia Virus Vectors," *J. Virol*. 64(10):4851-4857 (1990).

Rodrigues, E.G., et al., "Efficient Induction of Protective Anti-Malaria Immunity by Recombinant Adenovirus," *Vaccine*, 16(19):1812-1817, (1998).

Rodrigues, E.G., et al., "Single Immunizing Dose of Recombinant Adenovirus Efficiently Induces CD8+ T Cell-Mediated Protective Immunity Against Malaria," *J. Immunol*. 158(3):1268-1274 (1997).

Rodrigues, M., et al., "Influenza and Vaccinia Viruses Expressing Malaria CD8+ T and B Cell Epitopes," *J. Immunol*. 153(I0):4636-4648 (1994).

Romero, P., et al., "Cloned Cytotoxic T Cells Recognize an Epitope in the Circumsporozoite Protein and Protect Against Malaria," *Nature*, 341: 323-326 (1989).

Rosenberg, S.A., et al., "Recombinant Fowlpox Viruses Encoding the Anchor-Modified gp100 Melanoma Antigen can Generate Antitumor Immune Responses in Patients with Metastatic Melanoma," *Clin. Cancer Res.*, 9(8): 2973-2980 (2003).

Rothel, J.S., et al., "Sequential Nucleic Acid and Recombinant Adenovirus Vaccination Induces Host-protective Immune Responses Against *Taenia ovis* infection in Sheep," *Parasite Immunology* 19:221-227 (1997).

Rowland-Jones, S., et al., "HIV-specific Cytotoxic T-cells in HIV-exposed but Uninfected Gambian Women," *Nature Medicine* 1(1): 59-64 (1995).

Safety of and Immune Response to a DNA HIV Vaccine (pGA2/JS7) Boosted With a Modified Vaccinia HIV Vaccine (MVA/HIV62) in Healthy Adults. National Institute of Allergy and Infectious Diseases [online], Sep. 2006 [retrieved on Mar. 7, 2007], Retrieved from the Internet <URL:http://www.clinicaltrials.gov>.

Safety of and Immune Response to a DNA HIV Vaccine Followed by an Adenoviral Vector HIV Vaccine in Healthy Adults. National Institute of Allergy and Infectious Diseases [online], Jan. 2007 [retrieved on Mar. 1, 2007], Retrieved from the Internet <URL:http://www.clinicaltrials.gov>.

Schneider, J., et al., "A Prime-Boost Immunisation Regimen Using DNA Followed by Recombinant Modified Vaccinia Virus Ankara Induces Strong Cellular Immune Responses Against the *Plasmodium falciparum* TRAP Antigen in Chimpanzees," *Vaccine*, 19(32):4595-4602 (2001).

Schneider, J., et al., "DNA Followed by Recombinant Vaccinia Induces Cellular and Humoral Immune Responses Against a pre-erythrocytic Antigen of *Plasmodium falciparum* in Chimpanzees," *Immunol. Lett.*, 56/1-3: 291 (1997) (From *Poster Presentations Abstracts*, 1997, Abstract No. P.4.01.18).

Schödel, F., et al., "Immunity to Malaria Elicited by Hybrid Hepatitis B Virus Core Particles Carrying Circumsporozoite Protein Epitopes," *J. Exp. Med*. 180(3):1037-1046 (1994).

Sedegah, M., et al., "Protection against Malaria by Immunization with Plasmid DNA Encoding Circumsporozoite Protein," *Proc. Natl. Acad. Sci. USA* 91(21):9866-9870 (1994).

Seguin, M.C., et al., "Induction of Nitric Oxide Synthase Protects against Malaria in Mice Exposed to Irradiated *Plasmodium berghei* Infected Mosquitoes: Involvement of Interferon $\gamma$ and CD8+ T Cells,"*J. Exp. Med*. 180(1):353-358 (1994).

Sequence Alignment of SEQ ID No: 4 from U.S. Appl. No. 10/079,167 with Geneseq database ID No. AAR43245 from WO 93/20103-A. Entry date: May, 1994 Inventor: Elvin, et al.

Sequence Alignment of SEQ ID No. 2 from U.S. Appl. No. 10/079,167 with Geneseq database ID No. AAR43244 from WO 93/20103-A. Entry date: May 1994 Inventor: Elvin, et al.

Sequence Alignment of SEQ ID No. 6 from U.S. Appl. No. 10/079,167 with Geneseq database ID No. AAR43243 from WO 93/20103-A. Entry date: May 1994 Inventor: Elvin, et al.

Shah, K.V. and Howley, P.M., "Papillomaviruses." In *Fields Virology*, B.N. Fields, et al., eds. (PA: Lippincott-Raven Publishers) pp. 2077-2109 (1996).

Shaw, I., and Davison, T.F., "Protection From IBDV-induced Bursal Damage by a Recombinant Fowlpox Vaccine, fpIBD1, is Dependent on the Titre of Challenge Virus and Chicken Genotype," *Vaccine* 18:3230-3241 (2000).

Skinner, M.A., et al., "Fowlpox Virus as a Recombinant Vaccine Vector for use in Mammals and Poultry," *Expert Rev. Vaccines* 4(1):63-76 (2005).

Smith, C.L., et al., "Recombinant Modified Vaccinia Ankara Primes Functionally Activated CTL Specific for a Melanoma Tumor Antigen Epitope in Melanoma Patients with a High Risk of Disease Recurrence," *Int. J. Cancer* 113:259-266 (2005).

Somogyi, P., et al., "Fowlpox Virus Host Range Restriction: Gene Expression, DNA Replication, and Morphogenesis in Nonpermissive Mammalian Cells," *Virology* 197:439-444 (1993).

Stoute, J.A., et al., "A Preliminary Evaluation of a Recombinant Circumsporozoite Protein Vaccine Against *Plasmodium falciparum* Malaria," *N. Engl. J Med*. 336(2):86-91 (1997).

Sutter, G., et al., "A Recombinant Vector Derived From the Host Range-Restricted and Highly Attenuated MVA Strain of Vaccinia Virus Stimulates Protective Immunity in Mice to Influenza Virus," *Vaccine* 12(11):1032-1040 (1994).

Sutter, G. and Moss, B., "Nonreplicating Vaccinia Vector Efficiently Expresses Recombinant Genes," *Proc. Natl. ACAD. Sci. USA*, 89:10847-10851 (1992).

Syfpeithi Database, "Find Your Motif," [online], [retrieved on Sep. 1, 2006]. Retrieved from the Internet <URL:http://www.syfpeithi.de/Scripts/MHCServer.d11/FindYourMotif.htm>.

Tagawa, S.T., et al., "Phase I Study of Intranodal Delivery of a Plasmid DNA Vaccine for Patients with Stage IV Melanoma," *Cancer*, 98(1): 144-154 (2003).

Takada, K., et al., "Definition of an Epitope on Japanese Encephalitis Virus (JEV) Envelope Protein Recognized by JEV-specific Murine CD8+ Cytotoxic T Lymphocytes," *Arch Virol.*, 145: 523-534 (2000).

Tanghe, A., et al., "Improved Immunogenicity and Protective Efficacy of a Tuberculosis DNA Vaccine Encoding Ag85 by Protein Boosting," *Infect. Immun.* 69(5):3041-3047 (2001).

Tartaglia, J., et al., "NYVAC: A Highly Attenuated Strain of Vaccinia Virus," *Virology* 188(1):217-232 (1992).

Tartaglia, J., et al., "Protection of Cats against Feline Leukemia Virus by Vaccination with a Canarypox Virus Recombinant, ALVAC-FL," *J. Virol.* 67(4):2370-2375 (1993).

Tascon, R.E., et al., "Vaccination Against Tuberculosis by DNA Injection," *Nature Med.* 2(8):888-892 (1996).

Taylor, J. and Paoletti, E., "Fowlpox Virus as a Vector in Non-Avian Species," *Vaccine* 6:466-468 (1988).

Taylor, J., et al., "Protective Immunity Against Avian Influenza Induced by Fowlpox Virus Recombinant," *Vaccine* 6:504-508 (1988).

Taylor, J., et al., "Recombinant Fowlpox Virus Inducing Protective Immunity in Non-Avian Species," *Vaccine* 6(6):497-503 (1988).

The Chamberlain Declaration cited in the opposition proceedings of European Patent Application No. EP0979284. [Date singed by Opponent: Oct. 2, 2003; Date filed in EPO: Oct. 2, 2003].

The Gritz Declaration cited in the opposition proceedings of European Patent Application No. EP0979284. [Date signed by Opponent: Oct. 2, 2003; Date filed in EPO: Oct. 2, 2003].

The Schlom Declaration cited in the opposition proceedings of European Patent Application No. EP0979284. [Date signed by Declarant: Sep. 24, 2003; Date signed by Opponent: Oct. 2, 2003; Date filed in EPO: Oct. 2, 2003].

Thomson, S.A., et al., "Delivery of Multiple CD8 Cytotoxic T Cell Epitopes by DNA Vaccination," *J. Immunol.* 160:1717-1723 (1998).

Thomson, S.A., et al., "Recombinant Polyepitope Vaccines for the Delivery of Multiple CD8 Cytotoxic T Cell Epitopes," *J. Immunol.*, 157(2):822-826 (1996).

Timofeev, A.V., et al., "Immunological Basis for Protection in a Murine Model of Tick-Borne Encephalitis by a Recombinant Adenovirus Carrying the Gene Encoding the NS1 Non-Structural Protein," *J. Gen. Virol.* 79:689-695 (1998).

Timofeyev, A.V., et al., "Recombinant Adenovirus Expressing the NS1 Nonstructural Protein of Tick-Borne Encephalitis Virus: Characteristics of Immunological Basis of Antiviral Effect," *Vopr. Virusol.* 42:219-222 (1997). (English Abstract attached.).

Tomiyama, H., et al., "Different Effects of Nef-Mediated HLA Class I Down-Regulation on Human Immunodeficiency Virus Type 1-Specific CD8+ T-Cell Cytolytic Activity and Cytokine Production," *J. Virol.*, 76(15): 7535-7543 (2002).

Tonini, T., et al., "Current Approaches to Developing a Preventative HIV Vaccine," *Curr. Opin. Investig. Drugs*, 6(2):155-162 (2005).

Tsang, K.Y., et al., "Generation of Human Cytotoxic T Cells Specific for Human Carcinoembryonic Antigen Epitopes From Patients Immunized With Recombinant Vaccinia-CEA Vaccine," *J. Natl. Cancer Inst.* 87(13):982-990 (1995).

Tsuji, M., et al., "CD4+ Cytolytic T Cell Clone Confers Protection Against Murine Malaria," *J. Exp. Med.* 172(5):1353-1357 (1990).

Tsukamoto, K., et al., "Dual-Viral Vector Approach Induced Strong and Long-Lasting Protective Immunity against Very Virulent Infectious Bursal Disease Virus," *Virology* 269(2):257-267 (2000).

van Baren, N., et al., "Tumoral and Immunologic Response After Vaccination of Melanoma Patients with an ALVAC Virus Encoding MAGE Antigens Recognized by T Cells," *J. Clin. Oncol.*, 23(35): 9008-9021 (2005).

Van den Eynde, B. and Van der Bruggen, P., "Peptide Database," *Cancer Immunity*, Mar. 2001, online, retrieved from the Internet on Jun. 23, 2003. <URL:http://cancerimmunity.org/peptidedatabase/tcellepitopes.htm>.

Vasmatzis, G., et al., "Computational Determination of Side Chain Specificity for Pockets in Class I MHC Molecules," *Molecular Immunology*, 33(16): 1231-1239 (1996).

Vuola, J.M., et al., "Differential Immunogenicity of Various Heterologous Prime-Boost Vaccine Regimens Using DNA and Viral Vectors in Healthy Volunteers, " *J. Immunol.*, 174(1): 449-455 (2005).

Walker, B.D., et al., "Long-term Culture and Fine Specificity of Human Cytotoxic T-Lymphocyte Clones Reactive with Human Immunodeficiency Virus Type 1," *Proc. Natl. Acad. Sci. USA* 86:9514-9518 (1989).

Wang, M., et al., "Active Immunotherapy of Cancer with a Nonreplicating Recombinant Fowlpox Virus Encoding a Model Tumor-associated Antigen," *J. Immunol.* 154(9):4685-4692 (1995).

Wang, R., et al., "Induction of CD4+ T Cell-dependent CD8+ Type 1 Responses in Humans by a Malaria DNA Vaccine," *Proc. Natl. Acad. Sci. USA* 98(19):10817-10822 (2001).

Wang, X., et al., "Cellular Immune Responses to Helper-Free HSV-1 Amplicon Particles Encoding HIV-1 gp120 are Enhanced by DNA Priming," *Vaccine*, 21(19-20): 2288-2297 (2003).

Warnier, G., et al., "Induction of a Cytolytic T-cell Response in Mice with a Recombinant Adenovirus Coding for Tumor Antigen P815A" *Int. J. Cancer* 67(2):303-310 (1996). (Abstract only).

Watson, J.C. and Peter, G., "General Immunization Practices," in *Vaccines*, Plotkin, S.A. and Orenstein, eds., (W.B. Saunders) pp. 47-73 (1999).

Whitton, J.L., et al., "A "String-of-Beads" Vaccine, Comprising Linked Minigenes, Confers Protection from Lethal-Dose Virus Challenge," *Journal of Virology*, 67(1): 348-352 (1993).

Wiley, J.A., et al., "Production of Interferon-γ by Influenza Hemagglutin in-Specific CD8 Effector T Cells Influences the Development of Pulmonary Immunopathology," *Am. J. Pathol.* 158(1): 119-130 (2001).

Wizel, B., et al., "Irradiated Sporozoite Vaccine Induces HLA-B8-Restricted Cytotoxic T Lymphocyte Responses against Two Overlapping Epitopes of the *Plasmodium falciparum* Sporozoite Surface Protein 2," *J. Exp. Med.* 182(5):1435-1445 (1995).

Woodberry, T., et al., "Prime Boost Vaccination Strategies: CD8 T Cell Numbers, Protection, and Th1 Bias," *J. Immunol.*, 170: 2599-2604 (2003).

Xiang, Z.Q., et al., "Induction of Genital Immunity by DNA Priming and Intranasal Booster Immunization with a Replication-Defective Adenoviral Recombinant," *J. Immunol.* 162: 6716-6723 (1999).

Yang, Y., et al., "Upregulation of Class I Major Histocompatibility Complex Antigens by Interferon γ is Necessary for T-cell-mediated Elimination of Recombinant Adenovirus-infected Hepatocytes In Vivo," *Proc. Natl. Acad. Sci. USA*, 92: 7257-7261 (1995).

Yellen-Shaw, A.J., et al., "Point Mutation Flanking a CTL Epitope Ablates In Vitro and In Vivo Recognition of a Full-Length Viral Protein," *J. Immunol.*, 158(7): 3227-3234 (1997).

Zajac, P., et al., "Phase I/II Clinical Trial of a Nonreplicative Vaccinia Virus Expressing Multiple HLA-A0201-Restricted Tumor-Associated Epitopes and Costimulatory Molecules in Metastatic Melanoma Patients," *Human Gene Therapy*, 14(16): 1497-1510 (2003).

Zhu, X., et al., "Functions and Specificity of T Cells Following Nucleic Acid Vaccination of Mice Against *Mycobacterium tuberculosis* Infection," *J. Immunol.* 158:5921-5926 (1997).

Zhu, M., et al., "Specific Cytoltic T-Cell Responses to Human CEA from Patients Immunized with Recombinant Avipox-CEA Vaccine," *Clin. Cancer Res.*, 6: 24-33 (2000).

Zorn, E. and Hercend, T., "A Natural Cytotoxic T Cell Response in a Spontaneously Regressing Human Melanoma Targets a Neoantigen Resulting from a Somatic Point Mutation," *Eur. J. Immunol.* 29:592-601 (1999).

Notification of Transmittal of the International Search Report and the Written Opinion of the International Searching Authority, or the Declaration, International Search Report and the Written Opinion in PCT Application No. PCT/GB2006/001902, 17 pages, mailed Oct. 4, 2006.

International Preliminary Report on Patentability and International Preliminary Report on Patentability in International Application No. PCT/GB2006/001902, 9 pages, date of issuance Nov. 23, 2007.

Notification of Transmittal of the International Search Report and the Written Opinion of the International Searching Authority, or the Declaration, International Search Report and the Written Opinion in PCT Application No. PCT/GB2006/001774, 16 pages, mailed Jan. 2, 2006.

International Preliminary Report on Patentability in International Application No. PCT/GB2006/001774, 7 pages, date of issuance Nov. 13, 2007.

Nov. 2, 2000, Requirement for Restriction / Election, U.S. Appl. No. 09/454,204.
May 7, 2001, Response to Restriction Requirement, U.S. Appl. No. 09/454,204.
May 7, 2001, Preliminary Amendment, U.S. Appl. No. 09/454,204.
Jul. 16, 2001, Requirement for Restriction / Election, U.S. Appl. No. 09/454,204.
Oct. 17, 2001, Response to Restriction Requirement, U.S. Appl. No. 09/454,204.
Dec. 21, 2001, Preliminary Amendment, U.S. Appl. No. 09/454,204.
Jan. 14, 2002, Requirement for Restriction / Election, U.S. Appl. No. 09/454,204.
Feb. 20, 2002, Examiner Interview Summary Record (PTOL-413), U.S. Appl. No. 09/454,204.
Apr. 12, 2002, Response to Restriction Requirement, U.S. Appl. No. 09/454,204.
Jul. 1, 2002, Office Action—Non-Final, U.S. Appl. No. 09/454,204.
Sep. 16, 2002, Response after Non-Final Action, U.S. Appl. No. 09/454,204.
Oct. 11, 2002, Supplemental Response, U.S. Appl. No. 09/454,204.
Dec. 30, 2002, Office Action—Non-Final, U.S. Appl. No. 09/454,204.
May 6, 2003, Response after Non-Final Action, U.S. Appl. No. 09/454,204.
Jun. 3, 2003, Examiner Interview Summary, U.S. Appl. No. 09/454,204.
Jun. 25, 2003, Supplemental Response, U.S. Appl. No. 09/454,204.
Aug. 25, 2003, Examiner's Amendment Communication, U.S. Appl. No. 09/454,204.
Aug. 25, 2003, Notice of Allowance, U.S. Appl. No. 09/454,204.
Mar. 23, 2004, Restriction Requirement, U.S. Appl. No. 10/079,167.
Jul. 21, 2004, Reply to Restriction Requirement, U.S. Appl. No. 10/079,167.
Nov. 3, 2004, Office Action—Non Final, U.S. Appl. No. 10/079,167.
May 3, 2005, Amendment, U.S. Appl. No. 10/079,167.
Nov. 4, 2005, Office Action—Final, U.S. Appl. No. 10/079,167.
Jan. 5, 2006, Amendment After Final, U.S. Appl. No. 10/079,167.
Feb. 27, 2006, Advisory Action Before the Filing of and Appeal Brief, U.S. Appl. No. 10/079,167.
May 4, 2006, Amendment, U.S. Appl. No. 10/079,167.
Jun. 29, 2006, Office Action—Non Final, U.S. Appl. No. 10/079,167.
Nov. 29, 2006, Amendment, U.S. Appl. No. 10/079,167.
Feb. 26, 2007, Office Action—Final, U.S. Appl. No. 10/079,167.
Oct. 18, 2007, Office Action—Non-Final, U.S. Appl. No. 10/079,167.
Feb. 19, 2008, Amendment, U.S. Appl. No. 10/079,167.
Jun. 5, 2008, Office Action—Final, U.S. Appl. No. 10/079,167.
Feb. 16, 2006, Restriction Requirement, U.S. Appl. No. 10/653,624.
Mar. 15, 2006, Response to Restriction Requirement, U.S. Appl. No. 10/653,624.
Apr. 27, 2006, Office Action—Non-Final, U.S. Appl. No. 10/653,624.
Sep. 27, 2006, Reply Under 37 C.F.R. §1.111, U.S. Appl. No. 10/653,624.
Dec. 12, 2006, Office Action—Final, U.S. Appl. No. 10/653,624.
Jul. 18, 2007, Amendment, U.S. Appl. No. 10/653,624.
Oct. 1, 2007, Office Action—Non-Final, U.S. Appl. No. 10/653,624.
Apr. 3, 2008, Office Action—Non-Final, U.S. Appl. No. 10/653,624.
Jul. 2, 2004, Preliminary Amendment U.S. Appl. No. 10/686,943.
Feb. 16, 2006, Restriction Requirement, U.S. Appl. No. 10/686,943.
May 16, 2006, Response to Restriction Requirement, U.S. Appl. No. 10/686,943.
Jul. 5, 2006, Office Action—Non-Final, U.S. Appl. No. 10/686,943.
Nov. 6, 2006, Amendment, U.S. Appl. No. 10/686,943.
Dec. 21, 2006, Interview Summary/Supplemental Amendment, U.S. Appl. No. 10/686,943.
Apr. 2, 2007, Office Action—Non-Final, U.S. Appl. No. 10/686,943.
Sep. 4, 2007, Amendment, U.S. Appl. No. 10/686,943.
Nov. 14, 2007, Office Action—Final, U.S. Appl. No. 10/686,943.
Dec. 3, 2007, Interview Summary, U.S. Appl. No. 10/686,943
May 13, 2008, Reply, U.S. Appl. No. 10/686,943.
Jul. 17, 2008, Office Action—Final, U.S. Appl. No. 10/686,943.
Jul. 30, 2009, Communication Re: Appeal, U.S. Appl. No. 10/686,973.
Mar. 13, 2006, Restriction Requirement, U.S. Appl. No. 10/833,744.
Apr. 13, 2006, Reply to Restriction Requirement, 10/833,744.
May 22, 2006, Office Action—Non-Final, U.S. Appl. No. 10/833,744.
Sep. 22, 2006, Reply Under 37 C.F.R. §1.111, U.S. Appl. No. 10/833,744.
Dec. 15, 2006, Office Action—Final, U.S. Appl. No. 10/833,744.
Jan. 12, 2007, Interview Summary, U.S. Appl. No. 10/833,744.
May 15, 2007, Amendment, U.S. Appl. No. 10/833,744.
Aug. 10, 2007, Office Action—Non-Final, U.S. Appl. No. 10/833,744.
Nov. 19, 2007, Amendment, U.S. Appl. No. 10/833,744.
Jan. 8, 2008, Notice of Allowance, U.S. Appl. No. 10/833,744.
Feb. 7, 2008, Miscellaneous Action with SSP, U.S. Appl. No. 10/833,744.
Feb. 7, 2008, Remarks on the Notice of Allowability/Interview Summary, U.S. Appl. No. 10/833,744.
Mar. 21, 2008, Examiner Interview Summary Record, U.S. Appl. No. 10/833,744.
Mar. 13, 2006, Restriction Requirement, U.S. Appl. No. 10/833,439.
Apr. 13, 2006, Reply to Restriction Requirement, U.S. Appl. No. 10/833,439.
May 11, 2006, Office Action—Non-Final, U.S. Appl. No. 10/833,439.
Oct. 11, 2006, Reply Under 37 C.F.R. §1.111, U.S. Appl. No. 10/833,439.
Jan. 16, 2007, Office Action—Final, U.S. Appl. No. 10/833,439.
May 16, 2007, Amendment, U.S. Appl. No. 10/833,439.
Aug. 10, 2007, Office Action—Non-Final, U.S. Appl. No. 10/833,439.
Jan. 10, 2008, Amendment, U.S. Appl. No. 10/833,439 2907.
Apr. 2, 2008, Office Action—Non-Final, U.S. Appl. No. 10/833,439.
Jun. 27, 2008, Reply, U.S. Appl. No. 10/833,439.
Nov. 21, 2008, Notice of Allowance, U.S. Appl. No. 10/833,439.
Mar. 13, 2006, Restriction Requirement, U.S. Appl. No. 10/833,745.
Apr. 24, 2006, Interview Summary, U.S. Appl. No. 10/833,745.
May 18, 2006, Reply to Restriction Requirement, U.S. Appl. No. 10/833,745.
Jun. 21, 2006, Office Action—Non-Final, U.S. Appl. No. 10/833,745.
Oct. 26, 2006, Amendment, U.S. Appl. No. 10/833,745.
Jan. 30, 2007, Office Action—Non-Final, U.S. Appl. No. 10/833,745.
Jun. 4, 2007, Amendment, U.S. Appl. No. 10/833,745.
Aug. 22, 2007, Office Action—Final, U.S. Appl. No. 10/833,745.
Nov. 5, 2007, Amendment After Final, U.S. Appl. No. 10/833,745.
Feb. 19, 2008, Office Action—Final, U.S. Appl. No. 10/833,745.
Oct. 22, 2008, Reply, U.S. Appl. No. 10/833,745.
Jan. 15, 2009, Office Action—Final, U.S. Appl. No. 10/833,745.
Oct. 16, 2009, Restriction Requirement, U.S. Appl. No. 12/221,498.
Dec. 2, 2008, Restriction Requirement, U.S. Appl. No. 11/986,294.
Dec. 15, 2004, Restriction Requirement, U.S. Appl. No. 10/088,677.
Jan. 18, 2005, Amendment, U.S. Appl. No. 10/088,677.
Apr. 8, 2005, Miscellaneous Action with SSP, U.S. Appl. No. 10/088,677.
May 9, 2005, Amendment, U.S. Appl. No. 10/088,677.
Jul. 29, 2005, Miscellaneous Action with SSP, U.S. Appl. No. 10/088,677.
Aug. 29, 2005, Amendment, U.S. Appl. No. 10/088,677.
Nov. 4, 2005, Miscellaneous Action with SSP, U.S. Appl. No. 10/088,677.
Dec. 16, 2005, Amendment, U.S. Appl. No. 10/088,677.
Mar. 21, 2006, Office Action—Non-Final, U.S. Appl. No. 10/088,677.
Jul. 31, 2006, Amendment, U.S. Appl. No. 10/088,677.
Mar. 16, 2007, Petition Decision, U.S. Appl. No. 10/088,677.
May 30, 2007, Office Action—Final, U.S. Appl. No. 10/088,677.
Sep. 4, 2007, Amendment, U.S. Appl. No. 10/088,677.
Feb. 5, 2008, Office Action—Non-Final, U.S. Appl. No. 10/088,677.
Jun. 9, 2008, Amendment, U.S. Appl. No. 10/088,677.
Sep. 30, 2008, Office Action—Final, U.S. Appl. No. 10/088,677.
Dec. 28, 2004, Restriction Requirement, U.S. Appl. No. 10/856,118.

Jun. 6, 2005, Reply to Restriction Requirement, U.S. Appl. No. 10/856,118.
Aug. 9, 2005, Office Action—Non-Final, U.S. Appl. No. 10/856,118.
Feb. 13, 2006, Amendment, U.S. Appl. No. 10/856,118.
May 3, 2006, Office Action—Final, U.S. Appl. No. 10/856,118.
Jul. 17, 2006, Amendment After Final, U.S. Appl. No. 10/856,118.
Aug. 2, 2006, Advisory Action, U.S. Appl. No. 10/856,118.
Oct. 20, 2006, Office Action—Non-Final, U.S. Appl. No. 10/856,118.
Feb. 20, 2007, Amendment, U.S. Appl. No. 10/856,118.
May 18, 2007, Notice of Allowance and Interview Summary, U.S. Appl. No. 10/856,118.
Sep. 28, 2005, Restriction Requirement, U.S. Appl. No. 11/008,653.
Dec. 5, 2005, Reply to Restriction Requirement, U.S. Appl. No. 11/008,653.
Jan. 13, 2006, Office Action—Non-Final and Examiner Interview Summary, U.S. Appl. No. 11/008,653.
Apr. 17, 2006, Amendment, U.S. Appl. No. 11/008,653.
Jun. 16, 2006, Office Action—Final, U.S. Appl. No. 11/008,653.
Aug. 18, 2006, Amendment After Final, U.S. Appl. No. 11/008,653.
Oct. 10, 2006, Office Action—Non-Final, U.S. Appl. No. 11/008,653.
Apr. 12, 2007, Amendment, U.S. Appl. No. 11/008,653.
Jul. 12, 2007, Office Action—Final, U.S. Appl. No. 11/008,653.
Jun. 16, 2008, Amendment, U.S. Appl. No. 11/008,653.
Sep. 10, 2008, Office Action—Non-Final, U.S. Appl. No. 11/008,653.
Apr. 9, 2009, Examiner Interview Summary, U.S. Appl. No. 11/008,653.
Raghavan, M., et al., "MHC class I assembly: out and about," *Trends Immunol.*, 29(9): 436-443 (Sep. 2008).
Valmori, D., et al., "Modulation of Proteasomal Activity Required for the Generation of a Cytotoxic T Lymphocyte-defined Peptide Derived from the Tumor Antigen MAGE-3," *J.Exp.Med.*, 189(6): 895-905 (Mar. 15, 1999).
Palmowski, M. J., "Strategies for the Induction of Epitope-Specific Polyvalent CTL Responses," Published doctoral dissertation, University of Oxford, Oxford, England, Trinity Term (Apr.-Jun. 2002).

* cited by examiner

Figure 1
Tyrosinase 1-9 (A2)
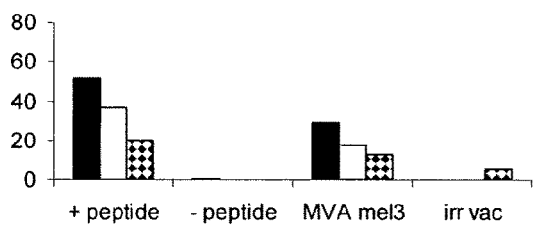
Mage-3 271-279 (A2)
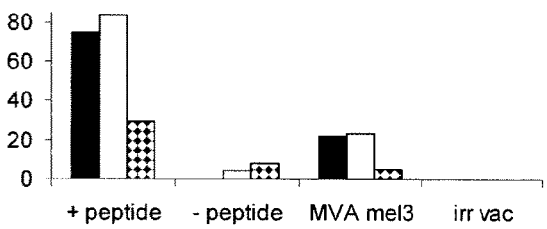
Melan-A 26-35 (A2)
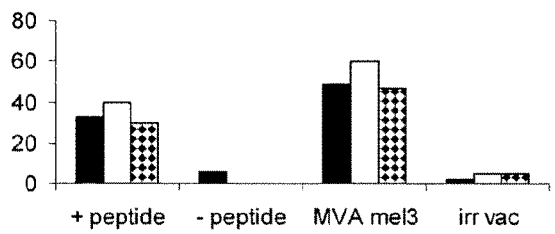
Mage-1 155-169 (A1)
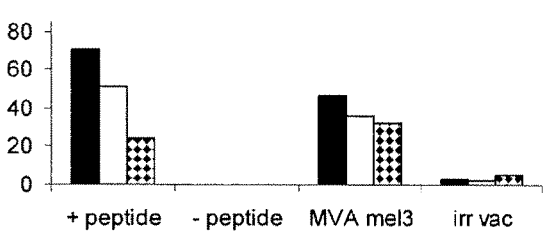
Tyrosinase 369-377 (A2)
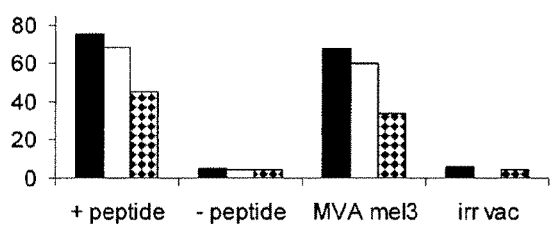
NY-ESO-1 157-166 (A2)
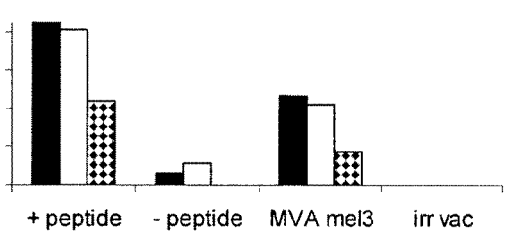
Mage-3 167-175 (A1)
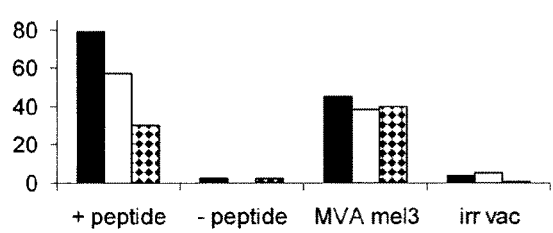
Flu NP 366-374 (H2-Db)
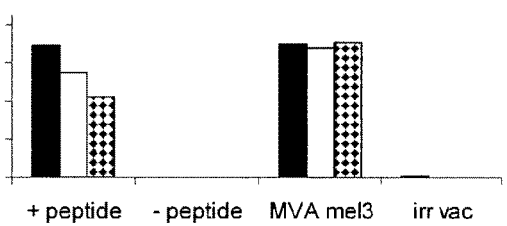

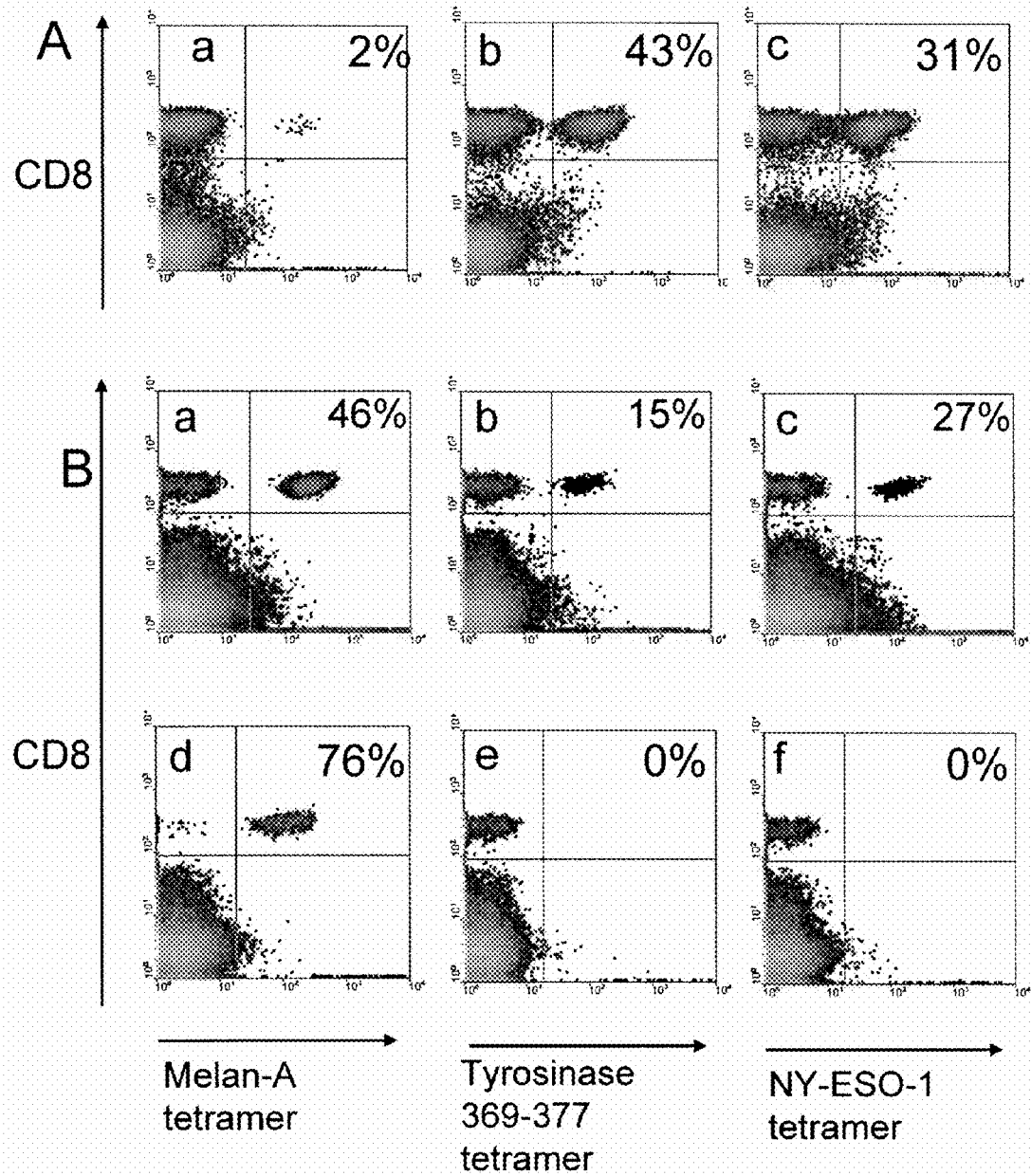

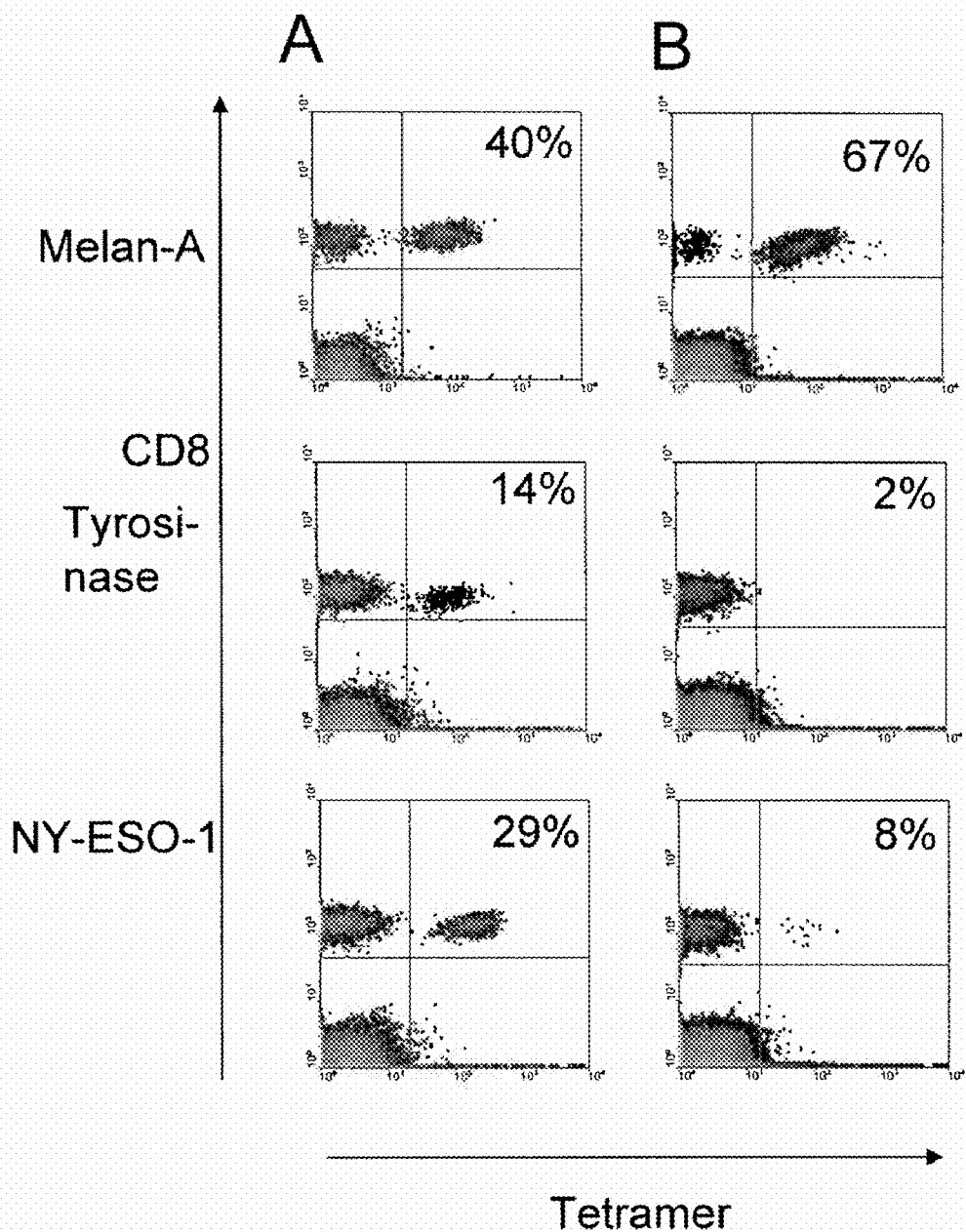

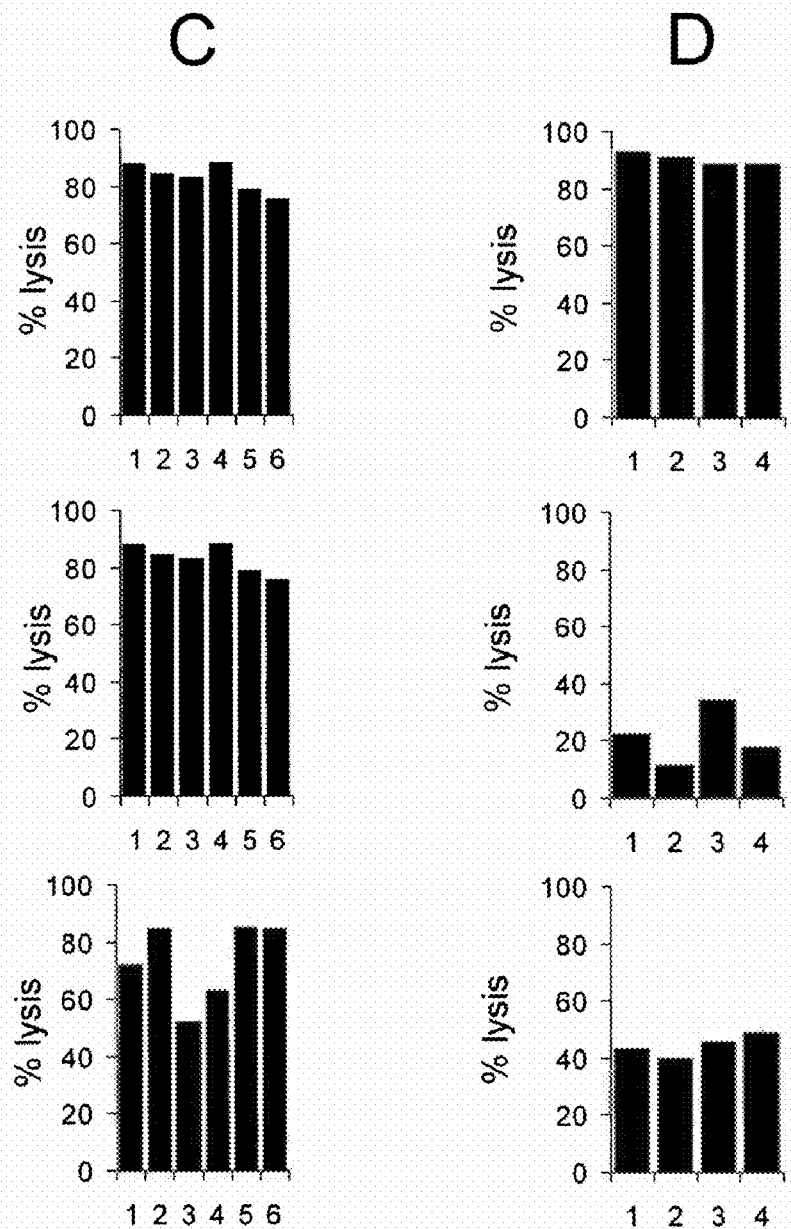

A) MVA.mel3 prime DC pulsed with mixed peptides boost
B) MVA.mel3 prime DC pulsed with single peptides boost

MATERIALS AND METHODS RELATING TO IMPROVED VACCINATION STRATEGIES

RELATED APPLICATIONS

This application is a divisional of U.S. application Ser. No. 10/485,074, filed Jan. 28, 2004, abandoned, which is the U.S. National Stage of International Application No. PCT/GB02/03496, filed on Jul. 30, 2002, published in English, which claims priority under 35 U.S.C. §119 or 365 to Great Britain Application No. 0118532.1, filed Jul. 30, 2001.

The present invention relates to materials and methods for improving vaccination strategies. Particularly, but not exclusively, the invention relates to "prime-boost" vaccination protocols in which the immune system is induced by a priming composition and boosted by administration of a boosting composition. The invention further relates to novel tetrameric soluble class I MHC/peptide complexes as a tool for directly monitoring vaccination regimens and determining novel epitopes.

Recent advances in our ability to monitor frequency of antigen CTL responses in ex-vivo assays are rapidly improving our capacity to compare different vaccination protocols. In particular, the use of tetrameric soluble class I MHC/peptide complexes (tetramers) provides an opportunity to greatly accelerate development of new vaccines by allowing rapid and accurate analysis of human CTL responses [1-3].

It has become clear that heterologous prime-boost vaccination protocols, based on repeated injections of non-cross reactive vectors encoding the same antigenic protein, result in strong CTL responses, probably due to focusing of the immune response towards epitopes contained within the recombinant target proteins [4]. Recent results have demonstrated that combination of priming with plasmid DNA and boosting with recombinant defective vaccinia virus MVA generate high levels of specific immunity [5-10].

Alphaviruses have been extensively studied as viral vectors in vaccination protocols [11-15]. The replication incompetent alphavirus, Semliki Forest Virus (SFV), has proven to be capable of inducing antibodies and CTL directed against the encoded foreign antigens [14,15]. The small size of the SFV genome [16] makes this virus a very attractive vector for vaccination strategies, as expression of a small number of viral structural proteins maximise the chances of generating an immune response specific to recombinant proteins, rather than to viral structural proteins.

Several studies have demonstrated that viruses and tumour cells evade specific immune responses by mutating or deleting antigenic proteins [17,18]. In order to minimise the generation of virus or tumour antigen loss variants, vaccine induced immune responses should be specific to a broad range of different epitopes, possibly encoded by distinct proteins. This rationale has led to the generation of vaccines encoding strings of CTL epitopes, aimed at simultaneously expanding CTL with different specificity. Vaccination of A2 transgenic mice has shown that multiple epitopes encoded within poly-epitope constructs can each prime specific CTL, suggesting the feasibility of this approach for immunotherapy clinical trials [19-22]. However, due to the technical limitations of assays for directly monitoring CTL responses in these mice, evidence is lacking that polyvalent constructs are capable of expanding CTL of many specificities to effective levels.

There is hope that poly-epitope vaccines will be capable of inducing broad based cytotoxic T lymphocyte (CTL) responses in humans. The administration of a plurality of epitopes is aimed at simultaneously expanding a CTL with different specificity. Although such polyvalent constructs have proven capable of simultaneously priming CTL of multiple specificities in animals which is clearly advantageous, it remains unclear whether they are capable of subsequently boosting each of these CTL responses to effective levels.

It is known that some epitopes are more efficient at raising an immune response than others. Some epitopes may be described as dominant, i.e. they provoke a strong CTL response, while others may be described as subdominant in that they provoke a weaker response. However, when trying to raise an immune response to a broad range of epitopes it is important that the subdominant epitopes are not overlooked in favour of more dominant epitopes.

During the priming stage of a vaccine regimen the more dominant epitopes provoke a greater CTL response than the weaker epitopes. This means that after an initial priming event to a plurality of epitopes, the CTL response is inevitably greater for the more dominant species and weaker for the subdominant species. However, the present inventors have found that the situation is made worse when the same plurality of epitopes is administered as a poly-epitope construct during the boosting phase. This appears to be true even when the poly-epitope is provided in a different vector/vehicle than the priming phase. The inventors have found that during the boosting stage, the CTL response to the more dominant epitopes is increased at a greater rate than the CTL response to the subdominant epitope, to the extent that the expansion of the CTL response to the subdominant epitopes is significantly reduced. This means that the CTLs raised to the dominant epitopes are expanded further at the expense of the CTLs raised to the subdominant epitopes. As a consequence, the proportion of CTLs raised to the dominant epitopes is increased whereas the proportion of CTLs raised to the subdominant epitopes is only marginally increased. This means that the boosting phase narrows the immune response by favouring proliferation of CTL expanded in the initial priming stage.

The present inventors have surprisingly determined a novel prime-boost regimen that helps to overcome the potentially negative effect of the boosting phase on a plurality of dominant and subdominant epitopes.

Remarkably, the inventors have found that a broad CTL response can be more uniformly boosted to effective levels if, following the priming stage, the epitopes are used individually to boost the response as opposed to being administered as a single poly-epitope construct. By boosting with the individual epitopes, the inventors have found that the CTLs raised against the dominant epitopes are not boosted at the expense of the CTLs raised against the subdominant epitopes. Rather, they are boosted equally.

Specifically, and as exemplified below, the inventors have used DNA and viral vectors encoding a string of melanoma epitopes, to demonstrate that prime-boost vaccinations result in the expansion of a narrow CTL repertoire. At the boosting step the inventors found that CTL competition for recognition of cells presenting the poly-epitope construct skews the response towards those CTL expanded more efficiently during priming. In contrast, the inventors have found that simultaneous expansion of CTL specific to dominant and subdominant determinants is obtained when APCs were presenting the epitopes separately during the boosting phase. This could be accomplished, for example, by injecting a mixture of viruses each encoding a separate antigen or by injecting a mixture of APC presenting the epitopes separately.

Thus, the invention provides a method of inducing a specific but broad based CTL response to a plurality of epitopes, where poly-epitope constructs are used in the priming phase of a vaccination regimen but immunogens encoding or comprising the epitopes individually are used for the boosting phase.

The invention also provides a heterologous prime-boost vaccination regimen where epitopes in the boosting phase are presented to the immune system in a different way than in the priming stage. This is explained in more detail below.

The present invention arises from the determination that the boosting phase is considerably more effective in inducing a specific but broad based CTL response to a plurality of epitopes if those epitopes are administered individually.

Thus, if an individual has already been primed by a plurality of epitopes, the invention provides a method of boosting the previously induced (primed) immune response comprising administering the plurality of epitopes individually, i.e. separately, on separate constructs or carried by separate vehicles.

In all aspects of the invention described herein, a plurality of epitopes may be taken to any number of epitopes greater than 2, more preferably, greater than 4 and still more preferably greater than 7. Of the plurality of epitopes, at least two, more preferably four and even more preferably seven epitopes will be different i.e. comprise a different amino acid sequence or be recognised by different antibodies. However, it is also preferably that the plurality of epitopes comprise many epitopes in the order of tens or hundreds. It is likely that some of these epitopes will be very similar and may cross-react.

Thus, if an individual has been infected by, or in some way come in contact with i.e. been exposed to, a pathogen (e.g. virus, bacteria etc) or a tumour, then the individual's immune system will have been naturally primed against a plurality of epitopes presented by the pathogen or tumour. However, this initial priming of the immune system may well be insufficient for the individual to mount an effective defense against the pathogen or tumour. However, in accordance with the present invention, the already primed immune response may be, boosted by administering the plurality of epitopes individually, i.e. separately, carried by separate constructs (peptide or nucleic acid) or separate vehicles. Thus, in this context, the present invention has vast therapeutic potential.

Although it would be possible to detect whether an individual had been primed to a particular epitope, i.e. through exposure to a pathogen or as a result of a tumour, this step would not be necessary.

In order to save time, cost and trouble, it would be preferable to treat every patient suspected of having been primed to a plurality of epitopes by exposure to a pathogen or a tumour as a primed patient.

Accordingly, in a first aspect of the present invention, there is provided a method for boosting an immune response in an individual, said individual having been previously primed against or exposed to at least one of said plurality of epitopes, preferably all of said plurality of epitopes, said method comprising administering to the individual a plurality of constructs, each encoding or comprising one of said plurality of epitopes. The construct may be a nucleic acid sequence capable of encoding a peptide comprising the epitope in question or it may be a peptide or protein/polypeptide comprising the epitope which can be administered directly. The nucleic acid sequence may be DNA, RNA or cDNA capable of encoding a peptide comprising one or more of the epitopes in question. Whether the construct is nucleic acid sequence encoding the peptide or a peptide itself, it is preferable to use a vehicle to carry the construct so that is can be efficiently presented to the individual's immune system. Preferably, the constructs are each presented or carried by separate vehicles such as a nucleic acid expression vector, e.g. a viral vector, or APC, e.g. dendritic cells or lymphocytes e.g. B cells. The vehicles may also act as adjuvants to help with the inducing immune response. The APCs may be used to express peptide constructs or they may be pulsed prior to administration.

The method in accordance with the first aspect of the present invention, may further comprise administering a "second" or further boosting composition. This composition will also comprise individual constructs, each comprising one of said plurality of epitopes. Again, the constructs may be peptides or nucleic acid sequences capable of encoding said peptides.

The administration of a second or further boosting composition has the benefit of not only further boosting the individuals immune response to the administered epitopes but also providing a "first" boost to any epitopes present in the medicament that had not been already primed naturally by the individual through exposure to the pathogen or tumour. In other words, the second/further boosting composition ensures that any epitopes presented in the medicament ("first" boosting composition) that the individual had not previously been exposed to, would effectively be boosted for the first time.

Alternatively, the present invention may be used to immunise an individual against a pathogen or tumour associated antigen, i.e. as a preventative vaccine. In this situation, the individual's immune system must first be primed by a plurality of epitopes characteristic of the pathogen and then boosted to help the immune system raise an effective defense against the pathogen. This is known as a prime-boost regimen. However, as described above, the inventors have found that to maximise the immune response against each and every one of the epitopes, the epitopes must be administered individually in the boosting stage. Further, the inventors have also determined that a heterologous prime-boost regimen is preferable to the homologous prime-boost methods already described in the art. Thus, it also preferable to administer the plurality of epitopes during the boosting stage using separate vehicles, e.g. viral vectors, that are different to and non cross-reactive with vehicles which may have been used in the priming stage.

Thus, in a second aspect of the present invention, there is provided a method of inducing an immune response, preferably a CD8+ T cell immune response, to a plurality of epitopes in an individual, said method comprising the steps of administering to the individual a priming composition comprising a construct encoding or comprising said plurality of epitopes and then administering a boosting composition which comprises a plurality of individual constructs each comprising one of said plurality of epitopes.

In accordance with the second aspect, the construct may be a peptide (protein/polypeptide) or a nucleic acid sequence encoding said peptide. it is also preferably, that the constructs are administered using a vehicle capable of efficiently displaying the epitopes to the individual's immune system. Thus, where the construct is a nucleic acid sequence, this may be contained within a nucleic acid expression vector, i.e. a plasmid or viral vector. These vectors may likewise be contained within a cell such as an Antigen Presenting Cell (APC).

Where the construct is a peptide, it may be preferable to use a cell, more preferably an APC as a vehicle as these cells are capable of displaying peptides efficiently to the immune system. Examples of APCs include dendritic cells and lymphocytes.

The administration of the constructs to an individual using vehicles is described in more detail below.

The priming composition may comprise one or more nucleic acid vectors, each containing nucleic acid encoding a plurality of epitopes. Alternatively, the priming composition may comprise peptides or antigens containing a plurality of epitopes.

In this second aspect, the priming composition comprises a string of epitopes, i.e. a polyepitope construct. However, the method may alternatively include the administration of one or more constructs encoding or comprising one or more of the plurality of epitopes. However, in this situation, it is preferable that the prime-boost regimen is a heterologous prime-boost regimen. In other words, if the priming composition comprises individual epitopes, the boosting composition preferably carried or presents its individual epitopes using different and non-cross reactive vehicles.

For example, where nucleic acid constructs are used different viral vectors may be used in the priming and boosting phase. Likewise, for peptide constructs, different APC cells may be used between the priming and boosting phase, e.g. B cells for priming and dendritic cells for boosting.

This is a preferred embodiment of the invention and it must be appreciated that homologous prime-boost prime-boost regimens are also within the scope of the present invention, particularly when using peptide constructs.

It is also preferred that all priming nucleic acid constructs are recombinant constructs for example, any genetic constructs like recombinant viral constructs, DNA constructs, RNA constructs, or cells transfected or transduced with such constructs. Further the priming composition may comprise separate peptides or proteins and cells that are extra- or intracellularly loaded with such peptides or proteins. The peptides may form part of a fusion construct with a carrier protein or adjuvant. These may be produced as fusion proteins.

Where the boosting or priming compositions comprise peptides or proteins, these may be delivered using Antigen Presenting Cells (APCs) for example dendritic cells or lymphocytes (B cells), pulsed with peptide and/or protein (including intracellular delivery of peptides or proteins into the APC). The APCs once pulsed with peptide or protein may also be infected by virus in order to help activate the APC, i.e. the virus in this case acts as an adjuvant for the peptide.

Particles such as sepharose beads or chitine beads may also be used to mimic APCs and display peptide/MHC complexes and co-stimulatory molecules for stimulation of the immune system.

Exosomes or other subcellular bodies derived from APCs may also be pulsed with peptide and/or protein (including intracellular delivery of peptides or proteins into the exosomes) for delivery of the peptide epitopes.

It is also possible to administer the peptide or protein directly into the individual preferably at separate locations. The peptide or protein administered in this way is preferably accompanied by an adjuvant in either the priming or boosting phases.

Where a nucleic acid vector is provided as a vehicle, it is preferable that the nucleic acid encoding the epitopes is operably linked to regulatory sequences for production of said antigen in the individual by expression of the nucleic acid.

As the priming composition presents a plurality of epitopes, a broad but specific CTL response is induced by the individual's immune system.

In contrast to the priming composition, the boosting composition presents the epitopes always individually. This overcomes the problem determined by the inventors that pre-existing memory CTL responses significantly reduce CTL response to other epitopes contained within the same construct during the boosting phase.

The priming composition if used, or the boosting composition when using nucleic acid constructs, may further comprise any vehicle for carrying the nucleic acid construct encoding the epitopes e.g. a viral vector, such as adenovirus vectors, Herpes simplex virus vectors, vaccinia virus vector. The viral vector may be a modified, replication-deficient vector, e.g. modified virus Ankara (MVA), or it may be an avipox vector e.g. fowlpox, Canarypox and so on. Preferred vectors include the replication incompetent alphavirus Semliki Forest Virus (SFV). Other appropriate vectors will be apparent to those skilled in the art.

The priming composition may comprise DNA encoding the antigen. The DNA may be in the form of a circular plasmid that is not capable of replicating in mammalian cells. Expression of the antigen will preferably be driven by a promoter active in mammalian cells, e.g. cytomegalovirus immediate early (CMV IE) promoter.

The $CD8^+$ T cell immune response may be primed using a DNA vaccine, Ty-VLPs or recombinant modified Vaccinia virus Ankara (MVA). In the examples provided below, the inventors describe embodiments of the invention using a recombinant MVA naked plasmid DNA vaccinia virus, and semliki forest virus (SFV) during the priming phase. However, it will be apparent to the skilled person that other vectors, viral or otherwise, may equally be used.

As mentioned above, it is preferable to use a different, non-cross reactive vehicle, such as a nucleic acid expression vector, e.g. a viral vector, for displaying epitopes during the boosting phase than that used during the priming phase. In the examples provided below, plasmid DNA was used as a vehicle vector during the priming phase and vectors vaccinia, MVA and/or SFV were used as vehicles during the boosting phase. As multiple vectors will be used as vehicles during the boosting phase, these may be the same or different.

Thus, in accordance with the first and second aspect of the invention, there is provided a novel vaccination regimen that can be used as a method of vaccinating an individual against pathogens including self antigens or tumour antigens. Exemplified below are the use of NY-ESO-1, Tyrosinase and Melan-A antigens. However, other antigens will be known or may be determined by the skilled person.

Further, the invention has an important utility as a vaccination model for testing and establishing vaccination strategies or regimens. Thus, the vaccination model allows vaccination regimens to be established which maximise a specific but broad based CTL response to a plurality of epitopes.

It is usual to test vaccine regimens on laboratory animals such as mice prior to testing on humans in clinical trials. Transgenic mice have been used in the past to test responses to particular antigens or epitopes. It is important to provide a biological environment that is as equivalent to the human environment as is possible. Therefore, transgenic mice are produced which have the ability to express human MHC molecules. In the examples provided below, the inventors have used two forms of transgenic mice.

Firstly, they have used HHD A2 transgenic mice which express a transgenic monochain histocompatibility class I molecule in which the C terminus of the human $\beta 2m$ is covalently linked to the N terminus of a chimeric heavy chain (HLA-A2.1 $\alpha 1$-$\alpha 2$, H-$2D^b$ $\alpha 3$ transmembrane and intracytoplasmic domains). The H-$2D^b$ and mouse $\beta 2m$ genes of these mice have been disrupted by homologous recombination resulting in complete lack of serologically detectable cell surface expression of mouse histocompatibility class I molecules.

Secondly, the inventors have used A2-$K^b$ mice which express a chimeric heavy chain (HLA-A2.1 $\alpha 1$-$\alpha 2$, H-$2K^b$ $\alpha 3$ transmembrane and cytoplasmic domains) in non-covalent association with mouse $\beta 2m$.

Thus, both of these transgenic mice express a chimeric MHC where the α1 and α2 domains are derived from human A2 MHC and the α3 domain is from murine H-2K$^b$ or H-2D$^b$. These mice are referred to as A2 transgenic mice. However, the present invention may equally well be performed on HLA-A1, HLA-A3 or HLA-A4 transgenic mice, i.e. any other murine model expressing human class I molecule s in a similar way as A2 transgenic mice do.

Therefore, the invention further provides a method of testing a vaccination regime comprising the steps of administering a primary composition to a test animal, said primary composition comprising a nucleic acid encoding a plurality of epitopes under test, subsequently administering a boosting composition, said boosting composition comprising a plurality of nucleic acid vectors each containing one of the said plurality of epitopes under test; and determining the CTL response to each of the epitopes under test.

Preferably, the test animal will be a transgenic animal that provides an immune environment as close to the human immune environment as possible. The preferred test animal is an A2 transgenic mouse as described herein.

As discussed above, the priming vector preferably is a DNA plasmid or viral vector. However, the boosting vectors are preferably different to the priming vector. In a preferred embodiment the priming vector is DNA, and the boosting vector is selected from the group of vaccinia, MVA and/or SFV. SFV is the preferred vector for the boosting phase as the inventors have determined that excellent results are achieved when used following DNA priming vector or with MVA as the boosting vector. SFV does not cross-react with MVA and therefore these immunogen vectors can be effectively used together. The inventors have also found that the nucleic acid constructs whether as part of a viral vector or not, may be administered in association with a mammalian cell, such that the antigens are presented on its surface. Such cells are known as Antigen Presenting Cells (APCs) when antigen is presented on their surface. Thus, the term APC includes cells such as tumour cells. The use of APCs to carry the construct is particularly preferable during the boosting stage. Thus, possible boosting reagents include APCs, such as dendritic cells or lymphocytes transfected or transduced with the viral or non-viral nucleic acid construct or tumour cells displaying antigen.

In particular embodiments of the first aspect of the present invention, administration of a priming composition is followed by boosting compositions, the priming composition and the boosting composition being different from one another, e.g. as exemplified below. However, a second and third boosting composition may be administered within the method of the present invention as mentioned above. In one embodiment, a triple immunisation regimen employs DNA expressing a plurality of epitopes; followed by SFV as a first boosting composition where a plurality of SFV vectors are used each comprising one of the plurality of priming epitopes; followed by MVA as a third boosting composition where a plurality of MVA vectors are used each comprising one of the plurality of priming epitopes. Alternatively, the SFV boosting composition may be administered after the MVA boosting composition.

Likewise, where peptides are administered directly, peptide pulsed APCs, exosomes or APC mimics may also be used for several sequential boosting steps. This may be achieved by sequential injections.

In all cases, it is preferable to administer (e.g. by injection) the priming and boosting composition several times to ensure successful delivery.

Priming with vectors expressing a plurality of epitopes can be followed by a mixture of recombinant virus (i.e. either SFV or MVA) comprising one or more of the plurality of priming epitopes and followed by a further boosting based on the injection of peptides, each, encoding one of the plurality of priming epitopes. The peptides will preferably be between 5 and 15 amino acids in length, more preferably between 5 and 12 amino acids in length, more preferably between 5 and 10 amino acids in length. 9 amino acid long peptides are preferred. The peptides may be naturally occurring or they may be synthetic.

In order to enhance the method of testing vaccination regimens or strategy, the inventors have appreciated that accurate, efficient and fast testing of the provoked CTL response is required. With this is mind, the present inventors have developed a novel tetramer based technique to directly monitor the frequency of HLA A2 restricted CTL expanded in vaccinated HLA A2 transgenic mice. In association with the first aspect of the present invention, this will greatly accelerate development of new vaccines by allowing rapid and accurate analysis of human CTL responses.

Specifically, the inventors have developed a technique for directly monitoring A2 restricted CTL responses in the blood of A2 transgenic mice by engineering chimeric A2 class I molecules containing the mouse H2K$^b$ alpha 3 domain. This technique allows accurate monitoring of the frequency of CTL induced by prime-boost regimens using poly-epitope constructs encoded within a number of different vectors and the correlation of the frequency of these CTL with their cytotoxic activity in vivo. This has the advantage of reducing the number of mice in each study considerably as they do not have to be killed for their CTL responses to be addressed.

Thus, in a further aspect of the invention, there is provided a multimeric MHC structure that is capable of detecting specific CTLs expanded following vaccination of an individual or test animal with one or more epitopes. The multimeric MHC structure comprises two or more MHC molecules, preferably four molecules, held together in a single structure by a binding member such as streptavidin. The streptavidin used here may be fluorescently labelled for the detection of the CTLs binding the tetramer. As a plurality of MHC molecules are held in close proximity, they can by effectively used to display the epitope of interest in the form of a peptide so as to detect CTLs raised to that epitope. If effectively primed, the CTLs will recognise the displayed peptide/epitope and bind to the structure. This binding can be detected by known techniques such as flow cytometry, usually in combination with labelled antibodies e.g. anti. CD8 antibodies.

However, the inventors have found that the use of these multimeric MHC structures, preferably tetramers, for testing the CTL responses in the vaccination model described above is limited as the MHC is of human origin whereas the test animal will be non-human, usually mouse, and therefore will have murine CD8 which does not effectively binding to human MHC.

To overcome this problem, the inventors have devised a chimeric multimeric MHC structure where the human α3 domain of the MHC is replaced with a murine α3 domain.

As the α3 domain binds the CD8 molecule, the chimeric multimeric MHC structure is more efficient at detecting the CTL response to the epitope under test than the non-chimeric structure.

Therefore, the invention further provides a chimeric multimeric MHC structure comprising at least two human MHC molecules held in close proximity by a binding member, wherein each MHC molecule contains an altered α3 domain so as to represent a murine α3 domain instead of a human α3 domain. Preferably, the human α3 domain is replaced by a murine α3 domain. The chimeric multimeric MHC structure may also be complexed with peptides displaying the epitope under test.

The murine α3 domain may be inserted into the human MHC to replace the human α3 domain, by creating a fusion protein, or by mutating the human α3 domain by insertion, deletion, or substitution of amino acids or nucleotides encoding amino acids characteristic of the murine α3 domain. Ideally, the chimeric MHC is produced as a fusion protein where nucleic acid encoding the human α1 domain and human α2 domains is expressed along with nucleic acid encoding the murine α3 domain. In this way a chimeric MHC fusion protein will be produced.

The multimeric chimeric MHC structure can then be associated with a peptide displaying the epitope under test. The number of peptides being displayed by the chimeric MHC will depend on the number of MHC molecules in the multimeric structure. The inventors have produced tetramers which will allow four peptides/epitopes to be displayed in close proximity. Thus, this structure can be used to detect the presence of a CTL response to the epitope in question. For example, the tetramer will display the peptide/epitope and when added to a biological sample (e.g. blood) obtained from the test animal, any CTLs recognising the epitope will bind to the tetramer with the aid of murine CD8. As the murine CD8 binds more successfully to murine α3 domain than human α3 domain, the binding of the CTL to the chimeric MHC tetramer according to the present invention is more stable than binding to a non-chimeric MHC tetramer.

The binding of the tetramer to the CTL can be detected by using, for example a fluorescently labelled tetramer. In addition, labelled CD8 antibody can be used to aid in the detection labelling and staining techniques are known to the skilled person.

As well as being extremely useful in monitoring the CTL response in accordance with the vaccination regimens mentioned above, the chimeric multimeric MHC structures can also be used to quickly and efficiently determine epitopes in a particular protein.

For example, A2 transgenic mice immunised with defined tumour or viral antigenic protein(s) encoded by DNA and/or recombinant viruses can be monitored for their ability to mount a specific CTL response by using the chimeric multimeric MHC class I molecules associated with peptides derived from the antigenic protein(s). This protocol will make possible the rapid identification of novel peptide epitopes encoded within antigenic proteins.

The inventors' findings are of importance for the design of optimised vaccines capable of simultaneously expanding high numbers of CTL specific for multiple epitopes. They are also important with regard to providing a vaccination model which allows quick, efficient and reliable testing of epitopes and allows design of the most efficient vaccination regimen.

The inventors have also devised a novel chimeric MHC multimer which can be used to efficiently detect a CTL response to a test epitope in a test animal.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

Table 1 Poly-CTL epitope construct (SEQ ID NO:2). The poly-CTL epitope gene (mel3) (SEQ ID NO:1) was constructed as a single string of epitopes. Mel3 cassette was cloned into four distinct vectors: naked DNA, vaccinia virus WR, MVA and SFV.

FIG. 1 efficient processing and presentation of mel3 CTL. HLA A2 and HLA A1 positive B cells were infected with mel3.MVA and used as targets of CTL clones specific to each epitope contained within the mel.3 poly-CTL construct. Specificity of each CTL clone and percentage of specific lysis are shown above each panel. Target cells were pulsed with relevant peptide (+ peptide), unpulsed (− peptide), infected either with mel3 MVA (MVA.mel3) or an irrelavant vaccinia (irr vac). Mouse NP 366-374 specific CTL were used as effectors cells against mouse MC57 fibroblasts infected with mel3.MVA.

Each bar corresponds to a different effector to target ratio: black bars 10:1, open bars 3:1 dotted bars 1:1.

Figure 2:
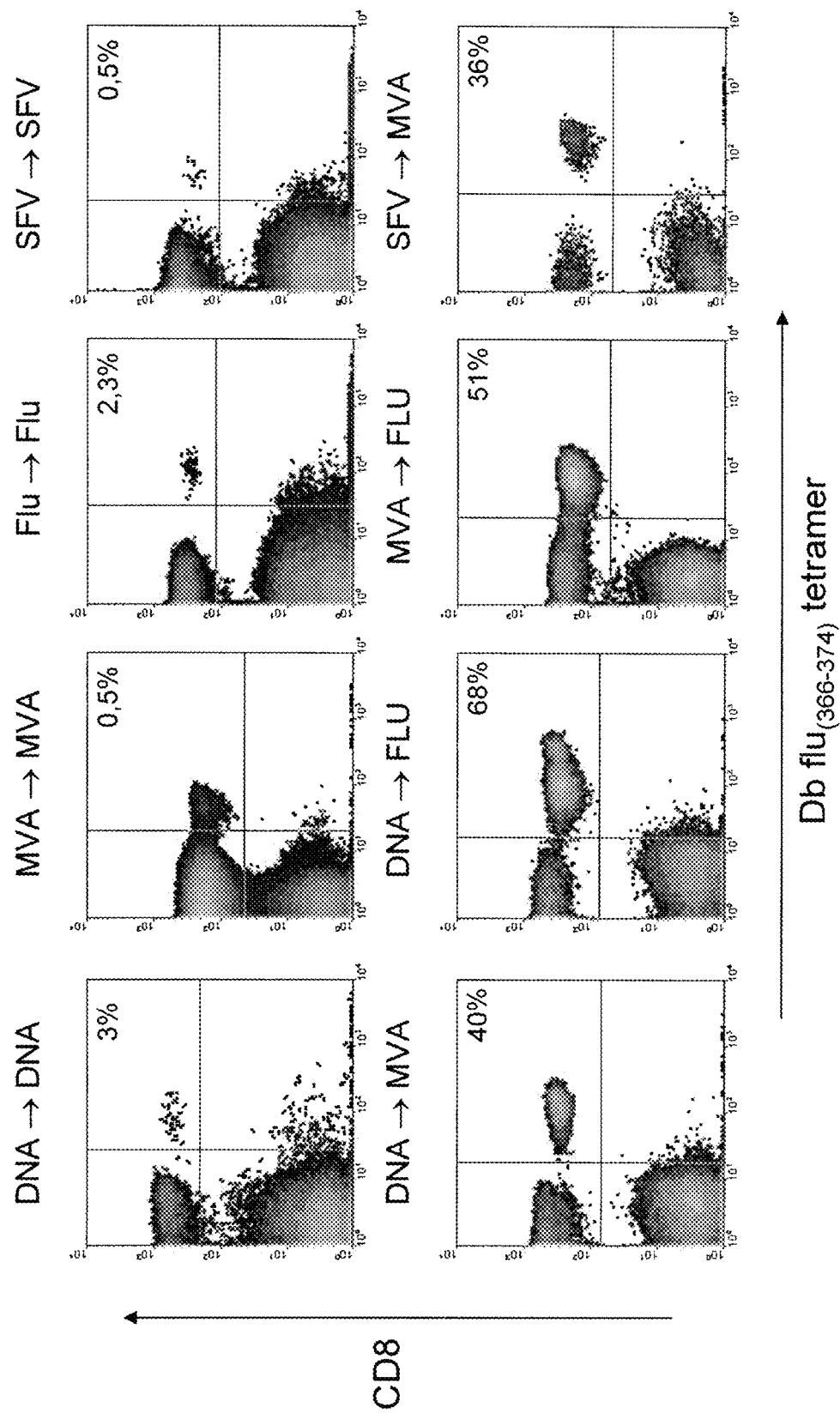

FIG. 2 Ex-vivo frequency of NP 366-374 specific CTL in mice immunised with homologous and heterologous prime boost vaccination strategies. Each panel corresponds to a different vaccination procedure.

Figure 3:
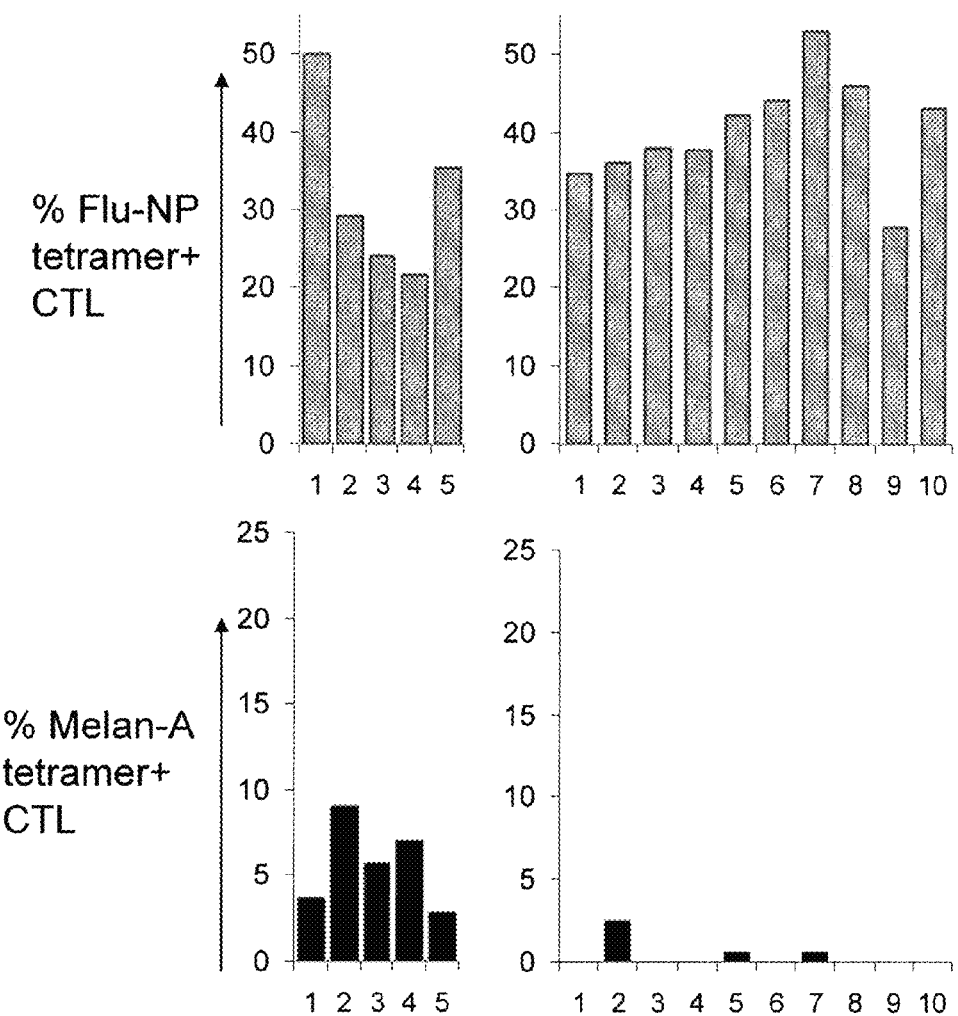

FIG. 3 Prime-boost of A2/Kb mice with DNA.mel3 followed by MVA.mel3.

A. Simultaneous generation of Db and A2 restricted CTL in A2/Kb transgenic mice. Mice were primed i.m. with DNA-mel3 and boosted 10 days later i.v. with MVA-mel3. Ex-vivo tetramer analysis of DB/NP366-374 and A2/melan-A 26-35 was carried out. Frequency of tetramer positive cells is shown in each vaccinated mouse after 3 days from MVA boost.

B. Effect of pre-existing memory CTL response specific to a single determinant contained within the poly-CTL epitope construct. A2/Kb mice were immunised i.n. with influenza virus and subsequently injected with DNA.mel3 followed by MVA.mel3. Ex-vivo tetramer analysis of Db/NP366-374 and A2/melan-A 26-35 was carried out. Frequency of tetramer positive cells is shown in each vaccinated mouse after 3 days from MVA boost.

Figure 4:
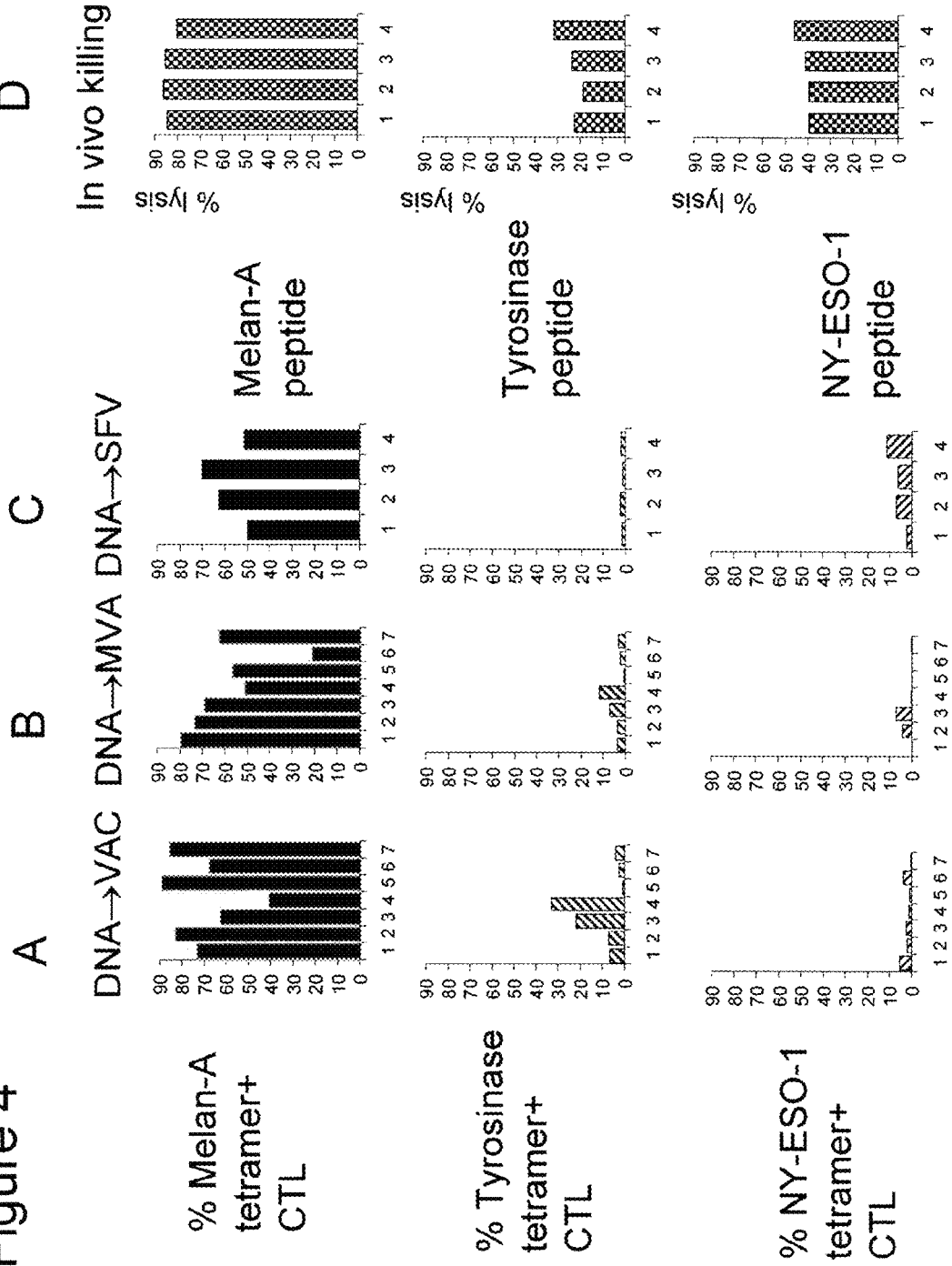

FIG. 4 Hierarchy of prime-boost vaccine driven CTL. HHD mice were primed with DNA.mel3 and boosted with either vac. Mel3 (A), MVA.mel3 (B) or SFV.mel.3 (C). Frequency of melan-A, tyrosinase and NY-ESO-1 specific responses were simultaneously measured by ex-vivo tetramer staining. DNA.mel3 primed SFV.mel3 boosted mice (group C) were injected with fluorochrome labelled splenocytes pulsed with either the melan-A, tyrosinase or NY-ESO-1 peptide. The percentage of in vivo killing is shown (D).

FIG. 5 Immunodominance of Melan-A specific CTL response can be overcome by poly-vaccinia-boosting or by adoptive transfer of in vitro infected splenocytes. DNA.mel3 primed HHD mice were either boosted with a mixture of vaccinia viruses encoding the full length tyrosinase and full length NY-ESO-1 (A). Alternatively, DNA mel3 primed HHD mice were injected either with three aliquotes of splenocytes separately infected in vitro with full length tyrosinase, full length NY-ESO-1 and mel3. Vaccinia (B, panels a, b and c) or with splenocytes infected with mel3 vaccinia (B, panels d, e and f). Frequency of melan-A, tyrosinase and NY-ESO-1 specific responses were simultaneously measured by ex-vivo tetramer staining.

FIG. 6 Poly-virus boosting overcomes the immunodominance of melan-$A_{26-35}$ specific CTL. DNA.mel3 primed HHD mice were boosted with either a mixture of vaccinia viruses encoding the full length tyrosinase, full length NY-ESO-1 and SFV.mel3 (A) or with SFV.mel3 (B). Frequencies of melan-$A_{26-35}$, tyrosinase$_{369-377}$ and NY-ESO-$1_{157-165}$ specific responses were simultaneously measured by ex-vivo tetramer staining. Staining of a single mouse out of six is shown. C and D: Each mouse was injected with fluorochrome labeled splenocytes pulsed with either the melan-$A_{26-35}$, tyrosinase$_{369-377}$ or NY-ESO-$1_{157-165}$ peptide and the % of in vivo lysis was calculated. Panel C corresponds to the in vivo killing in DNA.mel3 primed HHD mice boosted with a mixture of vaccinia viruses encoding the full length tyrosinase, full length NY-ESO-1 and SFV.mel3, while panel D corresponds to the in vivo killing in DNA.mel3 primed HHD mice boosted with SFV.mel3.

Figure 7:
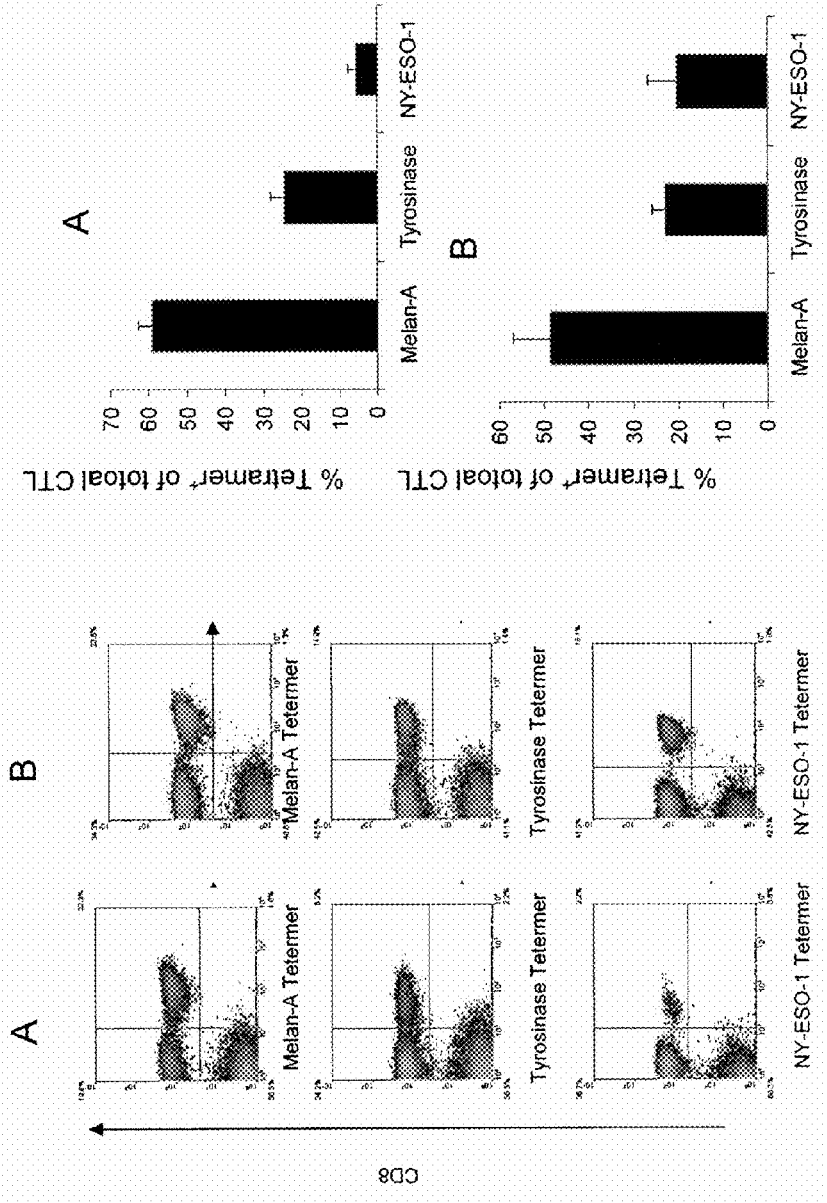

FIG. 7 The experiment shows A2K$^b$ tetramer stains from mice primed with MVA.mel3 and boosted with peptide pulsed dendritic cells (DCs). Two groups of mice are shown: Group A (three mice) received DCs pulsed with a mixture of 3 peptides (Melan-A, Tyrosinase and NY-ESO-1), and Group B (four mice) received a mixture of DCs pulsed with single peptides. On the left hand side of the figure, one individual response to three epitopes is shown from one mouse in each group. On the right hand side of the figure the average percentage of tetramer positive CTL in each group is shown. The error bars indicate the standard deviation of the mean. The experiment shows that peptide pulsed DCs can efficiently boost poly valent CTL responses primed by recombinant MVA (compare FIG. 4A, B and C) The experiment further demonstrates, that a mixture of separately peptide pulsed DCs for boosting is more efficient in boosting a poly-valent response when compared to DCs pulsed with a mixture of peptides.

DETAILED DESCRIPTION

Materials and Methods
Plasmid DNA Construct

The DNA vector pSG2, used throughout the study, was derived from pRc/CMV (Invitrogen, Paisley, UK) by removing the BamH1 fragment that contains the SV40 origin of replication and neomycin resistance marker and replacing the CMV promoter with a longer version of the same promoter containing intron A. The resulting plasmid contains the CMV promoter with intron A for expression in eukaryotic cells, followed by a multiple cloning site and the bovine growth hormone poly-A sequence. The plasmid is incapable of replication in mammalian cells. The gene encoding the mel3 sequence (Table 1) was introduced into the multiple cloning site using standard methods. Plasmid DNA for injection was purified using anion-exchange chromatography (Qiagen, Hilden, Germany) and diluted in phosphate buffered saline (PBS) at 1 mg DNA/ml.
Generation of Recombinant Vaccinia Virus and MVA Recombinant and non-recombinant MVA were routinely propagated and titrated in chicken embryo fibroblasts (CEF) grown in minimal essential medium supplemented with 10% foetal calf serum (FCS). Recombinant MVA were made as described by cloning the mel3 poly-epitope string (Table 1) into the vaccinia shuttle vector pSC11. CEF infected with MVA at a multiplicity of 0.05 pfu per cell were transfected with LIPOFECTIN® Transfection Reagent (Gibco) and shuttle plasmid as described[23]. The Vaccinia P7.5 promoter drives expression of the polyepitope. Recombinant MVA were plaque purified 8 times.

Vaccinia viruses (WR strain) expressing mel3, full length NY-ESO-1 (kindly provided by Dennis L. Panicali, Therion Biologics Corporation, MA 02142, USA) or tyrosinase were made by cloning the mel3 poly-epitope construct, the NY-ESO-1 and tyrosinase full length cDNA into the thymidine kinase gene using the vector pSC11 as previously described[24].

Generation of Recombinant SFV

The mel3 poly-epitope string was cloned into the transfer vector pSFV4.2-mel3. RNA produced from this vector was used to construct recombinant SFVmel3 particles. Recombinant SFV stocks were made and purified as described previously[16].
Generation of Human CTL Clones and CTL Assays Human CTL clones were isolated as described[25]. Briefly, tetramer/CD8 double positive stained CTL cultures were sorted as single cells into U-bottom 96-well plates, previously coated with anti-CD3 and anti CD28 both at 100 ng/ml in PBS, containing 10$^5$ irradiated B cells in Iscove's medium supplemented with 5% human serum, 100 U/ml IL-2. Proliferating clones were expanded to >10$^7$ cells and used as effectors for standard Cr$^{51}$ release assays. The inventors used JY B cells infected with MVA mel3 as targets for HLA A2 restricted CTL; XY B cells for HLA-A1 restricted epitopes and H-2b positive MC57 cells as targets for the D$^b$ restricted Influenza Nucleoprotein. We titrated CTL clones in three fold dilutions against targets
Tetramer Synthesis Fluorescent tetrameric HLA-A2.1/peptide complexes were synthesised as previously described[1]. A2-Kb/peptide complexes were synthesised in an analogous fashion using a chimeric heavy chain of α1 and α2 domain of the A2.1 molecule and the α3 domain, of the H-2 D$^b$ molecule with human β2-micro globulin.
Isolation of PBL and Tetramer Stains Fresh PBL were isolated from blood taken from tail vein using red cell lysis buffer (Invitrogen, Paisley, UK). For tetramer stains 3×10$^5$ cells were resuspended in 20 µl RPMI 1640 (Sigma, St Louis, Mo.) supplemented with 10% FCS. Cells were incubated with tetramer for 15 minutes at 37° C. PBL were then incubated with rat anti mouse CD8α (Pharmingen, San Diego, Calif.) for 15 minutes at 4° C. Cells were washed twice in PBS and resuspended in PBS for FACS-CAN™ Assay (Becton Dickenson, Mountain View, Calif.) analysis.
Animals and Immunization Protocols HHD mice express a transgenic monochain histocompatibility class I molecule in which the C terminus of the human β2m is covalently linked to the N terminus of a chimeric heavy chain (HLA-A2.1 α1-α2, H-2D$^b$ α3 transmembrane and intracytoplasmic domains) 20. The H-2D$^b$ and mouse β2m genes of these mice have been disrupted by homologous recombination resulting in complete lack of serologically detectable cell surface expression of mouse histocompatibility class I molecules. A2-K$^b$ mice express chimeric heavy chain (HLA-A2.1 alpha 1 alpha 2, H-2 K$^b$ alpha 3 transmembrane and cytoplasmic domains) in non-covalent association with mouse β2m. They additionally express a full set of C57BL/6-derived (H-2$^b$) class 1a and 1b mouse histocompatibility molecules[26]. All A2 transgenic mice used were bred in the inventors' animal facility. Female C57/BL6 mice 4-6 weeks old were obtained from Harlan Orlac (Shaws Farm, Blackthorn, UK). Plasmid DNA (25-50 µg/muscle) was dissolved in PBS and injected into each musculus tibialis under general anaesthesia. 10 days after DNA injection, mice were boosted with recombinant vaccinia viruses, which were diluted in PBS and 10$^6$-10$^7$ pfu and injected intravenously (i.v.) into the lateral tail vein. Alternatively freshly isolated spleen cells were separately infected (multiplicity of infection of 5) with mel3, full length tyrosinase and NY-ESO-1 vaccinia for 90 minutes in RPMI supplemented with 0.1% BSA at 37° C. Cells were washed 3 times and re suspended in sterile PBS at a concentration of 6×10$^7$ cells/ml combined and injected into lateral tail vein. Mice received 6×10$^6$ spleen cells.

Mice primed with influenza virus A (PR8) were infected by intra-nasal influenza injection (20 HAU/mouse). 30 days later mice were injected with DNA.mel3 followed by MVA.mel3, as described above. For priming or boosting with SFV-mel3 $10^8$ virus particles were diluted in sterile PBS and injected into the lateral tail vein.

In Vivo Killing

Freshly isolated spleen cells from HHD mice were separately incubated in RPMI medium with different peptides at a concentration of $10^{-6}$M for 2 h. Each cell pool was then labelled with a different concentration of carboxyfluorescein diacetate succinimidyl ester (CFSE, Molecular Probes, Eugene, Oregon) to allow simultaneous tracking of the different populations in vivo[27], Hermans, I. F., Yang, J. and Ronchese, F. Unpublished results. Labelled cells were pooled and injected at $10^7$ cells/mouse into the tail vein. A control population without peptide that had been labelled with 5-(and -6-)-(((4-chloromethyl)benzoyl)amino)tetramethyl-rhodamine (CELLTRACKER® Orange Fluorescent Probe, Molecular Probes, Eugene, Oregon) was co-injected to assess killing of peptide pulsed targets relative to unpulsed cells. Mice were bled at the time of injection of flurochrome labelled targets to determine their CTL frequencies to different epitopes. Disappearance of peptide/flurochrome labelled cells was tracked using FACS analysis of freshly isolated PBMC 5 h after the injection. Percentage killing was calculated relatively to the unpulsed population labelled with CELLTRACKER® Orange Fluorescent Probe. 100-(100×(% pulsed/% unpulsed)). WinMDI 2.8 and CellQuest™ 3.3 software was used to analyse the facs data.

Results

A string of 5 HLA-A2 and 2 HLA-A1 melanoma, epitopes was cloned into four distinct vectors: a) naked plasmid DNA (mel3. DNA); b) vaccinia virus (mel3-vaccinia); c) Modified Vaccinia Ankara virus (mel3. MVA); d) Semliki Forest Virus (mel3-SFV). To ensure monitoring of CTL responses restricted by human and mouse class I molecules, the inventors introduced an additional epitope from the influenza Nucleoprotein (NP) restricted by H-2 Db class I molecules. Since they had previously shown that presentation of amino-terminal NP366-374 epitope can be affected by neighbouring amino acid residues 24, the inventors decided to express the influenza NP 366-374 epitope at the carboxyl terminal end of the poly-epitope construct. Sequence of the poly-epitope constructs used in the paper are shown in Table 1.

Efficient Presentation of MVA Encoded Poly-Epitopes

Initial experiments were carried out, to compare the A2 binding affinity of each epitope contained within the mel.3 construct. The results of these experiments demonstrated that mel3 peptide epitopes had a broad range of binding affinities for A2 molecules. The Melan-A 26-35 peptide analogue 28 had the highest binding affinity, while the NY-ESO-1 157-165 and tyrosinase 1-9 peptides had a significantly lower affinity, as defined by their ability to inhibit at different concentrations presentation of the influenza Matrix epitope 58-66 (data not shown). The inventors and others have previously demonstrated that optimal flanking residues are important to ensure presentation of class I restricted epitopes 24,29. To establish that mel.3 peptide epitopes were properly processed, and to assess that competition for binding to A2 molecules did not impair CTL recognition of lower affinity epitopes, they infected target cells with mel.3 vaccinia and demonstrated that each of the 7 epitopes contained within the poly-epitope mel.3 cassette was simultaneously presented to specific CTL (FIG. 1). The inventors had previously shown that proteasome dependent degradation impairs presentation of the MAGE3 A2 epitope 271-279 [30]. It was therefore surprising to observe that infection of target cells with mel3 vaccinia was capable of sensitising them for lysis by MAGE3 271-279 specific CTL. Further experiments demonstrated that processing of the MAGE3 271-279 epitope contained within the mel3 construct, unlike its processing within the full length MAGE3 protein, was lactacystein resistant and TAP independent (data not shown), consistent with processing of mel.3 construct by Endoplasmic reticulum resident proteases.

Influenza NP 366-374 Specific CTL Responses in Mice Vaccinated with Poly-Epitope Encoded Vaccines Efficient presentation of the NP366-374 epitope by mel3 vaccinia infected cells prompted the inventors to assess in C57/B6 mice the ability of different vaccination strategies to induce a strong NP366-374 specific CTL response (FIG. 2). Ex-vivo monitoring of the NP specific CTL response was carried out in PBL using Db/Influenza NP366-374 tetramers. The inventors compared homologous vs heterologous prime boost vaccination protocols (FIG. 2), and analysed the kinetics of CTL induction by DNA or MVA priming (data not shown). The results of these experiments confirmed that heterologous vaccination strategies are capable of inducing long lasting vaccine driven CTL responses, with frequencies up to 100 times greater than frequencies obtained by strategies based on repeated injections of the same antigen delivery system (FIG. 2).

Expansion of A2 Restricted CTL in A2 Transgenic Mice

To test the ability of the mel.3 poly-epitope constructs to prime A2 restricted CTL responses in vivo, A2 transgenic mice were primed by DNA-mel.3 and boosted by MVA-mel.3, vaccinia mel.3, or SFV-mel3. Initial experiments were carried out using A2.1 transgenic mice, which express chimeric A2.1 molecules containing the Kb α3 domain, and endogenous $D^b$ and $K^b$ molecules (A2/Kb mice) [26]. To enable monitoring of the A2 restricted responses at the same time as the $D^b$ restricted Influenza NP366-374 response, the inventors employed novel A2/Kb tetramers, which were also capable of detecting the relevant CTL directly in PBL. Simultaneous staining with A2/Kb and $D^b$ tetramers demonstrated that priming of A2/Kb mice with DNA.mel3, followed by MVA-mel.3, induced melan-A 26-35 and Influenza NP 366-374 specific CTL responses (FIG. 3). In contrast, responses specific to other mel.3 epitopes were not detectable by ex vivo tetramer stainings (data not shown).

The ability to simultaneously monitor CTL responses against the influenza NP epitope 366-374 and melan-A epitope 26-35 prompted the inventors to study whether previous exposure to influenza virus may compromise the ability of prime-boost protocols to expand melan-A 26-35 specific CTL in A2-Kb mice. In order to generate a strong NP366-374 specific CTL response, A2 transgenic mice were immunised with influenza virus and subsequently received DNA.mel3 followed by MVA-mel3 (FIG. 3). The results of these experiments demonstrated that expansion of NP366-374 specific CTL, prior vaccination with mel3 poly-epitope constructs, significantly reduced the expansion of melan-A specific CTL (FIG. 3). The inhibitory effect of pre-existing flu specific CTL on the ability of mel3 prime-boost to induce melan-A specific CTL response (FIG. 3) raised the possibility that T cell interference during heterologous vaccination strategies may compromise the induction of a broad range immune response. The presence of endogenous mouse class I molecules significantly narrows the A2 restricted repertoire in A2 Kb mice, hence hampering the ability to study the interplay between A2 restricted CTL specific to different vaccine encoded determinants.

This reasoning led the inventors to monitor the hierarchy of vaccine driven CTL responses upon prime boost protocols in the A2 transgenic mice HHD [20]. HHD mice, unlike A2Kb transgenic mice, express A2.1 class I molecules linked to human β-2 microglobulin in a Db−/− and β-2m−/− background, and have a much larger A2 restricted T cell repertoire than A2/Kb transgenic mice [20].

Prime-Boost Vaccination of HHD Mice Induces Large Numbers of Melanoma Specific CTL Priming of HHD mice with DNA.mel3 led to the expansion of Melan-A specific CTL to frequencies detectable by ex-vivo tetramer staining in all vaccinated mice (data not shown). In contrast, expansion of NY-ESO-1 and tyrosinase specific CTL was only detectable in a small proportion of immunised mice, while responses to the Tyrosinase 1-9 and Mage3 271-279 were not detected in blood tetramer stainings (data not shown).

Additional experiments confirmed that NY-ESO-1 specific CTL responses were primed by DNA.mel3 injection, as shown by the significant NY-ESO-1 CTL response in DNA.mel3 primed mice boosted with vaccinia virus encoding the full length NY-ESO-1 (data not shown). In contrast, injection of NY-ESO-1 vaccinia virus, without priming with DNA.mel3, led to a much lower frequency of NY-ESO-1 CTL. Similar results were obtained upon injection of tyrosinase vaccinia in mice primed with DNA mel3 (data not shown).

The observation that the melan-A 26-35 specific CTL was the dominant vaccine driven CTL response after a single DNA vaccination, presented an opportunity to study the interplay between CTL specific to different vaccine encoded determinants in prime-boost vaccination protocols. The inventors observed that boosting of DNA.mel3 primed HHD mice with either vaccinia mel3 (FIG. 4a), MVA.mel3 (FIG. 4b), or SFV-mel3 (FIG. 4c), led to the expansion of melan-A specific CTL, up to 70-80% of total CD8+ T cells. Although responses specific to NY-ESO-1 and tyrosinase epitopes were significantly lower than the Melan-A specific responses, their frequencies ranged between 2 and 30% of CD8+ T cells, confirming that DNA priming and boosting with either replication competent (i.e. Vac.mel3) or incompetent viruses (MVA.mel.3 and SFV-mel3) significantly enhance the frequency of CTL specific to three distinct melanoma specific epitopes. The inventors confirmed that vaccine driven CTL were cytolytic, as shown by their ability to kill fluorochrome labelled splenocytes pulsed with relevant peptides in vivo (FIG. 4d). These results demonstrated that the cumulative response specific to melan-A, NY-ESO-1 and tyrosinase in HHD mice primed with DNA.mel3 and boosted with three distinct viral vectors accounted for the specificity of the majority of CD8+ population.

Competition of Vaccine Driven CTL for Mel.3 Expressing APC

Since the inventors demonstrated the inhibitory effect of a pre-existing flu memory CTL response on the ability to induce melan-A specific CTL (FIG. 3), they sought to study whether the high numbers of melan-A specific CTL, dominating the immune response after DNA priming, were capable of interfering with the expansion of NY-ESO-1 and tyrosinase specific CTL during the virus boosting.

It is known that competition for antigen recognition on the surface of antigen presenting cells leads to the immunodominance of higher frequency CTL populations [31-33]. The inventors reasoned that the higher numbers of melan-A CTL after DNA.mel 3 priming may lead either to rapid killing or shielding of mel3 vaccinia infected APC in vivo, resulting in a hampered stimulation of CTL specific to NY-ESO-1 and tyrosinase epitopes expressed by the same APC population.

This reasoning led them to assess whether a higher frequency NY-ESO-1 and tyrosinase specific CTL responses could be obtained by separating the APC expressing NY-ESO-1 and tyrosinase proteins from the APC expressing the mel3 construct. The results of these experiments confirmed this hypothesis, as shown by: 1) expansion of NY-ESO-1 and Tyrosinase specific CTL in DNA.mel3 primed mice and boosted with a mixture of vaccinia viruses, encoding the full length tyrosinase and full length NY-ESO-1 proteins (FIG. 5a); 2) simultaneous expansion of melan-A, NY-ESO-1 and tyrosinase specific CTL upon adoptive transfer into DNA.mel3 primed mice of three aliquotes of splenocytes infected ex-vivo with vaccinia viruses encoding full length NY-ESO-1, tyrosinase and mel3 construct (FIG. 5b, panels a, b and c), while adoptive transfer of splenocytes infected with mel3 vaccinia led to the expansion of Melan-A specific CTL (FIG. 5b panels d, e and f)

The Inventors have Demonstrated that Boosting of DNA.Mel3 primed mice with a mixture of recombinant viruses, encoding the full length tyrosinase, full length NY-ESO-1 and the mel3 construct, led to the simultaneous expansion of melan-$A_{26-35}$, NY-ESO-$1_{157-165}$ tyrosinase$_{369-377}$ specific CTL (FIGS. 6a and b). The identification of successful vaccination strategies to simultaneously expand large numbers of CTL with a broad specificity has important clinical applications, as we showed that T cell immunity induced by this type of optimised boosting strategies provides a more efficient in vivo killing of target cells than vaccinations based on poly-epitope prime boost strategies (FIG. 6 c and d).

Immunodominance of Melan-A specific CTL could be broken by separating the antigens during the boost. When separately infected splenocytes were used to boost a polyvalent response relevant peptides were separately presented and resulted in simultaneous expansion of Melan-A, Tyrasinase and NY-ESO specific CTL. To simplify this approach the inventors used peptide pulsed dentritic cells to boost an MVA.mel3 primed response. The cells used for boosting were either pulsed with a mixture of peptides (FIG. 7a) or separately pulsed (FIG. 7b). The inventors show that separate pulsing of APC is superior to pulsing APC with a mixture of peptides. This approach also demonstrates, that poly-epitope constructs encoded in vaccinia virus can efficiently prime and APC pulsed with peptide can efficiently boost a polyvalent CTL response.

Discussion

There is a tremendous momentum in vaccine development, as recent advances in the monitoring of antigen specific CTL responses in ex-vivo assays are rapidly improving our capacity to compare different vaccination protocols. In order to minimise the generation of tumour and virus antigen escape variants, it is important to ensure the expansion of vaccine driven CTL specific to several epitopes, including both dominant and subdominant determinants. Several papers have dissected the causes responsible for immunodominance of CTL specific to viral [34-36], and histocompatibility antigens [33,37, 38]. However, it remains to be established how optimal vaccine strategies can lead to the simultaneous expansion of CTL specific to dominant and subdominant epitopes.

To address these questions the inventors engineered 4 distinct vectors encoding a string of melanoma CTL epitopes (Table 1), and compared in A2 transgenic and wild type B6 mice the ability of different vaccination strategies to elicit vaccine specific CTL responses. In order to identify strategies capable of expanding CTL specific to dominant and subdominant determinants, peptide epitopes with high and low binding affinity for A2 molecules were linked in the same construct. More specifically, the inventors included the modified melan-A analogue 26-35, previously shown to have an enhanced immunogenicity in vivo [28] and the NY-ESO-1 peptide 157-165, shown to have a much lower binding affinity to A2 molecules [39] (Table 1).

Vaccine Driven CTL Hierarchy in Mel3 Vaccinated Mice

The inventors have developed a novel tetramer based technique to directly monitor the frequency of A2 restricted CTL expanded in A2 transgenic mice vaccinated in a prime-boost regimen. To increase the binding affinity of mouse CD8 to A2 molecules, they engineered A2 molecules containing the mouse H-2K$^b$ alpha 3 domain (A2/K$^b$ molecules), and demonstrated that tetrameric A2K$^b$ molecules have an increased staining efficiency for mouse A2 restricted CTL and can identify A2 restricted responses in a large proportion of A2 transgenic mice, as compared with tetrameric A2 molecules.

While studying the immune response in A2Kb mice, the inventors have demonstrated that expression of Db molecules results in a strong influenza NP366-374 specific response, which significantly impairs the expansion of CTL specific to other mel3 encoded epitopes. In order to study the interplay between A2 restricted CTL specific to different vaccine encoded determinants, the inventors immunised the A2 transgenic mice HHD 20, which, unlike A2Kb transgenic mice, express A2 molecules in a Db−/− background.

Although several papers have recently studied the immune response in A2 transgenic mice vaccinated with poly-epitope constructs 19,20,40, this is the first publication in which the hierarchy of poly-epitope vaccine driven CTL in A2 transgenic mice has been monitored by ex-vivo tetramer staining.

The inventors compared several vaccination strategies and confirmed that immunisations based on the injection of non-cross reactive vectors (heterologous prime-boost protocols) ensure higher levels of vaccine specific immune responses than immunisations based on the injections of homologous vectors (FIG. 2). The presence of neutralising antibodies against viral structural proteins and the presence of CTL specific to viral proteins may account for the lower CTL responses in mice vaccinated with repeated injections of the same virus, as compared with CTL frequencies upon vaccination with non-cross reactive vectors (FIG. 2). It has been suggested that the limited number of proteins encoded by plasmid DNA ensures that DNA priming focuses the immune response towards the recombinant protein, while virus boosting successfully expand this response, resulting in high levels of CTL specific to the recombinant protein. However, the inventors have shown that priming with either MVA.mel3 or SFV.mel3 led to a significant expansion of NP366-374 specific CTL upon boosting with influenza virus or MVA.mel3, respectively (FIG. 2), demonstrating that the ability to prime CTL is not unique to DNA vectors.

In HHD A2 transgenic mice, due to the lack of CTL restricted by endogenous mouse class I molecules, heterologous prime boost resulted in a tremendous expansion of melan-A specific CTL up to 90% of total CD8+ T cells (FIG. 4a), hence redirecting a large proportion of HHD mice's A2 restricted repertoire towards vaccine encoded CTL determinants. Several factors may contribute to the immunodominance of the melan-A specific CTL response. It is possible that a combination of an increased binding affinity for A2 molecules and for TCR, together with a favourable intracellular processing, may skew CTL responses towards the melan-A epitope 26-35 in DNA.mel3 primed mice.

Previous studies have shown that "suppression" of T cell responses specific to non dominant epitopes by T cell responses specific to dominant epitopes is observed only when both types of determinants are presented on the same APC [32,33,38]. Injection of large numbers of APC resulted in the expansion of T cells specific to the sub-dominant epitopes 41. The inventors have demonstrated that immunodominance of the melan-A epitope 26-35 was overcome by boosting strategies based on the injection of either a mixture of different recombinant viruses (FIG. 5a) or splenocytes infected in vitro by individual vaccinia viruses encoding full length proteins, rather than a poly-epitope construct (FIG. 5b).

Implications for Vaccination Strategies in Patients.

These results are of importance, since several clinical trials are currently using heterologous prime boost vaccination protocols with poly-epitope constructs. While the inventors confirm the ability of heterologous prime-boost protocols in eliciting large numbers of vaccine specific CTL, they demonstrate that during heterologous prime-boost protocols, frequency of immunodominant CTL responses is significantly expanded over frequency of CTL responses specific to less dominant determinants. Although there are numerous mechanisms which may account for a narrowing of the CTL repertoire which responds to a vaccine, the inventors' results are consistent with a model of immunodominance based on competition of T cells for antigen presenting cells (APCs) 32,33,38. It is worth noting that the injection of vac.mel3 into naïve mice induces lymphocytocis with a; shift of CD8+ frequency from 0.5% up to 30%, indicating a strong CTL response to the vaccinia virus. Of the CD8+ T cells induced in the blood as many as 50% are specific for Melan-A 26-35 (data not shown), demonstrating that melan-A 26-35 is one of the most immunodominant epitopes expressed by the virus amongst more than 200 vaccinia proteins responsible for the viruses' structure, transcription and replication. This observation has important clinical implications for the design of viral-based vaccines encoding the Melan-A epitope 26-35 The use of recombinant SFV in prime-boost protocols is very attractive, as the inventors have demonstrated that SFV can be used both as priming vector in combination with MVA (FIG. 2) and for boosting in combination with DNA (FIG. 4C). These results compliment a recently published report demonstrating in macaques the enhancement of simian immunodeficiency virus-specific immune responses induced by priming with recombinant SFV and boosting with MVA 11.

The inventors demonstrated that pre-existing memory CTL responses significantly reduce CTL responses specific to other epitopes contained within the same construct (FIG. 3b). As several groups have used immunodominant influenza peptide epitopes as positive controls during vaccination trials, the inventors' result suggest that DNA or virus based vaccines should not encode epitopes expressed by recurrent viruses, as pre-existing memory CTL response may compromise the induction of CTL responses specific to other vaccine encoded CTL determinants.

The inventors have further shown that T cell competition is likely to play a role in modifying T cell responses in prime-boost vaccination strategies. The inventors' work strongly suggests that simultaneous presentation of different epitopes to a skewed repertoire of primed CTL leads to dominant expansion of a single CTL specificity. However, boosting the primed response with APC separately presenting the epitopes results in comparable expansion of CTL of multiple specificities to effective levels in vivo.

Thus, the present inventors have, amongst other things provided a novel system for dissecting the ability of different vaccination protocols to optimally induce polyvalent A2-restricted CTL responses. In accordance with the present invention, methods for inducing a broad-based CTL response should restrict the use of polyvalent constructs to the priming phase and use separate vectors encoding individual epitopes, or separate proteins/peptides for the boosting phase.

References

1. Altman, J. D. et al. Phenotypic analysis of antigen-specific T lymphocytes. *Science* 274, 94-6. (1996).
2. Romero, P. et al. Ex vivo staining of metastatic lymph nodes by class I major histocompatibility complex tetramers reveals high numbers of antigen-experienced tumor-specific cytolytic T lymphocytes. *J Exp Med* 188, 1641-50. (1998).
3. Dunbar, P. R. et al. Direct isolation, phenotyping and cloning of low-frequency antigen-specific cytotoxic T lymphocytes from peripheral blood. *Curr. Biol* 8, 413-6. (1998).
4. Ramshaw, I. A. & Ramsay, A. J. The prime-boost strategy: exciting prospects for improved vaccination. *Immunol Today* 21, 163-5. (2000).
5. Schneider, J. et al. Enhanced immunogenicity for CD8+ T cell induction and complete protective efficacy of malaria DNA vaccination by boosting with modified vaccinia virus Ankara. *Nat Med* 4, 397-402. (1998).
6. Hanke, T., Schneider, J., Gilbert, S. C., Hill, A. V. & McMichael, A. DNA multi-CTL epitope vaccines for HIV and Plasmodium falciparum: immunogenicity in mice. *Vaccine* 16, 426-35. (1998).
7. Hanke, T. & McMichael, A. Pre-clinical development of a multi-CTL epitope-based DNA prime MVA boost vaccine for AIDS. *Immunol Lett* 66, 177-81. (1999).
8. Hanke, T. et al. Effective induction of HIV-specific CTL by multi-epitope using gene gun in a combined vaccination regime. *Vaccine* 17, 589-96. (1999).
9. Schneider, J. et al. Induction of CD8+ T cells using heterologous prime-boost immunisation strategies. *Immunol Rev* 170, 29-38. (1999).
10. Amara, R. R. et al. Control of a mucosal challenge and prevention of AIDS by a multiprotein DNA/MVA vaccine. *Science* 292, 69-74. (2001).
11. Nilsson, C. et al. Enhanced simian immunodeficiency virus-specific immune responses in macaques induced by priming with recombinant Semliki Forest virus and boosting with modified vaccinia virus Ankara. *Vaccine* 19, 3526-36. (2001).
12. Vidalin, O. et al. Use of conventional or replicating nucleic acid-based vaccines and recombinant Semliki forest virus-derived particles for the induction of immune responses against hepatitis C virus core and E2 antigens. *Virology* 276, 259-70. (2000).
13. Berglund, P., Fleeton, M. N., Smerdou, C. & Liljestrom, P. Immunization with recombinant Semliki Forest virus induces protection against influenza challenge in mice. *Vaccine* 17, 497-507. (1999).
14. Mossman, S. P. et al. Protection against lethal simian immunodeficiency virus SIVsmmPBj14 disease by a recombinant Semliki Forest virus gp160 vaccine and by a gp120 subunit vaccine. *J Virol* 70, 1953-60. (1996)
15. Zhou, X., Berglund, P., Zhao, H., Liljestrom, P. & Jondal, M. Generation of cytotoxic and humoral immune responses by nonreplicative recombinant Semliki Forest virus. *Proc Natl Acad Sci USA* 92, 3009-13. (1995).
16. Smerdou, C. & Liljestrom, P. Two-helper RNA system for production of recombinant Semliki forest virus particles. *J Virol* 73, 1092-8. (1999).
17. Dunbar, P. R. et al. A shift in the phenotype of melan-A-specific CTL identifies melanoma patients with an active tumor-specific immune response. *J Immunol* 165, 6644-52. (2000).
18. Marincola, F. M., Jaffee, E. M., Hicklin, D. J. & Ferrone, S. Escape of human solid tumors from T-cell recognition: molecular mechanisms and functional significance. *Adv Immunol* 74, 181-273 (2000).
19. Mateo, L. et al. An HLA-A2 polyepitope vaccine for melanoma immunotherapy. *J Immunol* 163, 4058-63. (1999).
20. Firat, H. et al. H-2 class I knockout, HLA-A2.1-transgenic mice: a versatile animal model for preclinical evaluation of antitumor immunotherapeutic strategies. *Eur J Immunol* 29, 3112-21. (1999).
21. Loirat, D., Lemonnier, F. A. & Michel, M. L. Multi-epitopic HLA-A*0201-restricted immune response against hepatitis B surface antigen after DNA-based immunization. *J Immunol* 165, 4748-55. (2000).
22. Sandberg, J. K. et al. Human immunodeficiency virus type 1 Nef epitopes recognized in HLA-A2 transgenic mice in response to DNA and peptide immunization. *Virology* 273, 112-9. (2000).
23. Carroll, M. W. et al. Highly attenuated modified vaccinia virus Ankara (MVA) as an effective recombinant vector: a murine tumor model. *Vaccine* 15, 387-94. (1997).
24. Gileadi, U., Gallimore, A., Van der Bruggen, P. & Cerundolo, V. Effect of epitope flanking residues on the presentation of N-terminal cytotoxic T lymphocyte epitopes. *Eur J Immunol* 29, 2213-22. (1999).
25. Dunbar, P. R. et al. Cutting edge: rapid cloning of tumor-specific CTL suitable for adoptive immunotherapy of melanoma. *J Immunol* 162, 6959-62. (1999).
26. Vitiello, A., Marchesini, D., Furze, J., Sherman, L. A. & Chesnut, R. W. Analysis of the HLA-restricted influenza-specific cytotoxic T lymphocyte response in transgenic mice carrying a chimeric human-mouse class I major histocompatibility complex. *J Exp Med* 173, 1007-15. (1991).
27. Barchet, W. et al. Direct quantitation of rapid elimination of viral antigen-positive lymphocytes by antiviral CD8(+) T cells in vivo. *Eur J Immunol* 30, 1356-63. (2000).
28. Men, Y. et al. Assessment of immunogenicity of human Melan-A peptide analogues in HLA-A*0201/Kb transgenic mice. *J Immunol* 162, 3566-73. (1999).
29. Velders, M. P. et al. Defined flanking spacers and enhanced proteolysis is essential for eradication of established tumors by an epitope string DNA vaccine. *J Immunol* 166, 5366-73. (2001).
30. Valmori, D. et al. Modulation of proteasomal activity required for the generation of a cytotoxic T lymphocyte-defined peptide derived from the tumor antigen MAGE-3. *J Exp Med* 189, 895-906. (1999).
31. Perkins, D. L., Berriz, G., Kamradt, T., Smith, J. A. & Gefter, M. L. Immunodominance: intramolecular competition between T cell epitopes. *J Immunol* 146, 2137-44. (1991).
32. Kedl, R. M. et al. T cells compete for access to antigen-bearing antigen-presenting cells. *J Exp Med* 192, 1105-13. (2000).
33. Pion, S. et al. On the mechanisms of immunodominance in cytotoxic T lymphocyte responses to minor histocompatibility antigens. *Eur J Immunol* 27, 421-30. (1997).
34. Belz, G. T., Stevenson, P. G. & Doherty, P. C. Contemporary analysis of MHC-related immunodominance hierarchies in the CD8+ T cell response to influenza A viruses. *J Immunol* 165, 2404-9. (2000).
35. Bousso, P., Lemaitre, F., Bilsborough, J. & Kourilsky, P. Facing two T cell epitopes: a degree of randomness in the primary response is lost upon secondary immunization. *J Immunol* 165, 760-7. (2000).

36. Chen, W., Anton, L. C., Bennink, J. R. & Yewdell, J. W. Dissecting the multifactorial causes of immunodominance in class I-restricted T cell responses to viruses. *Immunity* 12, 83-93. (2000).
37. Yewdell, J. W. & Bennink, J. R. Immunodominance in major histocompatibility complex class I-restricted T lymphocyte responses. *Annu Rev Immunol* 17, 51-88 (1999).
38. Grufman, P., Wolpert, E. Z., Sandberg, J. K. & Karre, K. T cell competition for the antigen-presenting cell as a model for immunodominance in the cytotoxic T lymphocyte response against minor histocompatibility antigens. *Eur J Immunol* 29, 2197-204. (1999).
39. Chen, J. L. et al. Identification of NY-ESO-1 peptide analogues capable of improved stimulation of tumor-reactive CTL. *J Immunol* 165, 948-55. (2000).
40. Woodberry, T. et al. Immunogenicity of a human immunodeficiency virus (HIV) polytope vaccine containing multiple HLA A2 HIV CD8(+) cytotoxic T-cell epitopes. *J Virol* 73, 5320-5. (1999).
41. Sandberg, J. K. et al. Superdominance among immunodominant H-2Kb-restricted epitopes and reversal by dendritic cell-mediated antigen delivery. *J Immunol* 160, 3163-9. (1998).

TABLE 1

| Nucleotide and amino acid sequence of mel.3 construct | Antigen | Epitope | Restriction |
|---|---|---|---|
| aga-tct-gcc-gcc-acc-- (SEQ ID NO: 3) | | | |
| atg-tta-cta-gct-gtt-ttg-tac-tgc-ctg- (SEQ ID NO: 4)<br>M L A V L Y C L (SEQ ID NO: 5) | Tyrosinase | 1-9 | (A2) |
| gaa-cta-gca-ggg-atc-ggc-ata-ttg-aca-gtg- (SEQ ID NO: 6)<br>E L A G I G I L T V (SEQ ID NO: 7) | Melan-A | 26-35(*) | (A2) |
| tat-atg-gat-gga-aca-atg-tcc-cag-gta- (SEQ ID NO: 8)<br>Y M D G T N S Q V (SEQ ID NO: 9) | Tyrosinase | 369-377 | (A2) |
| gga-tct- (SEQ ID NO: 10)<br>G S | (Linker) | | |
| gaa-gtc-gat-cca-atc-gga-cat-ttg-tac- (SEQ ID NO: 11)<br>E V D P I G H L Y (SEQ ID NO: 12) | Mage-3 | 167-175 | (A1) |
| ttc-ctg-tgg-ggt-cca-aga-gcc-ctc-gtt- (SEQ ID NO: 13)<br>F L W G P R A L V (SEQ ID NO: 14) | Mage-3 | 271-279 | (A2) |
| gaa-gca-gac-ccc-acc-gga-cac-tcc-tat- (SEQ ID NO: 15)<br>E A D P T G H S Y (SEQ ID NO: 16) | Mage-1 | 161-169 | (A1) |
| gga-tct- (SEQ ID NO: 17)<br>G S | (Linker) | | |
| cag-ctt-tcc-ctg-ttg-atg-tgg-atc-acg-cag-tgc-ttt-ctg- (SEQ ID NO: 18)<br>Q L S L L M W I T Q C F L (SEQ ID NO: 19) | NY-ESO-1 | 155-167 | (A2) |
| gct-tca-aat-gaa-aac-atg-gat-gct-atg-tga (SEQ ID NO: 20)<br>A S N E N M D A M (SEQ ID NO: 21) | Influenza Nucleoprotein | 366-374 | (Db) |

(*)this sequence corresponds to the peptide analogue modified at position 2 (Men et. al.)

The invention claimed is:

1. A polynucleotide sequence comprising a nucleotide sequence encoding a polypeptide that comprises SEQ ID NO:2, wherein the polypeptide is processed by Endoplasmic reticulum resident proteases when expressed in a cell.

2. A polynucleotide sequence according to claim 1 comprising SEQ ID NO:1.

3. A DNA plasmid comprising a polynucleotide sequence according to claim 1.

4. A recombinant Modified Vaccinia virus Ankara (MVA) virus comprising the polynucleotide sequence of claim 1.

5. A method of inducing a CD8+ immune response against melanoma-associated antigens in a subject comprising administering to said subject a DNA plasmid according to claim 3.

6. A method of inducing a CD8+ immune response against melanoma-associated antigens in a subject comprising administering to said subject a recombinant MVA virus according to claim 4.

7. A nucleic acid expression vector comprising the polynucleotide sequence of claim 1.

8. A viral vector comprising the polynucleotide sequence of claim 1.

* * * * *

SEQUENCE LISTING

<160> NUMBER OF SEQ ID NOS: 2

<210> SEQ ID NO 1
<211> LENGTH: 261
<212> TYPE: DNA
<213> ORGANISM: Artificial sequence
<220> FEATURE:
<223> OTHER INFORMATION: Poly-CTL epitope construct
<220> FEATURE:
<221> NAME/KEY: CDS
<222> LOCATION: (16)..(261)

<400> SEQUENCE: 1

```
agatctgccg ccacc atg tta cta gct gtt ttg tac tgc ctg gaa cta gca      51
               Met Leu Leu Ala Val Leu Tyr Cys Leu Glu Leu Ala
                 1               5                  10 ggg atc ggc ata ttg aca gtg tat atg gat gga aca atg tcc cag gta       99
```

```
                                                                         -continued
Gly Ile Gly Ile Leu Thr Val Tyr Met Asp Gly Thr Met Ser Gln Val
        15                  20                  25 gga tct gaa gtc gat cca atc gga cat ttg tac ttc ctg tgg ggt cca          147
Gly Ser Glu Val Asp Pro Ile Gly His Leu Tyr Phe Leu Trp Gly Pro
    30                  35                  40 aga gcc ctc gtt gaa gca gac ccc acc gga cac tcc tat gga tct cag          195
Arg Ala Leu Val Glu Ala Asp Pro Thr Gly His Ser Tyr Gly Ser Gln
45                  50                  55                  60 ctt tcc ctg ttg atg tgg atc acg cag tgc ttt ctg gct tca aat gaa          243
Leu Ser Leu Leu Met Trp Ile Thr Gln Cys Phe Leu Ala Ser Asn Glu
                65                  70                  75 aac atg gat gct atg tga                                                  261
Asn Met Asp Ala Met
                80

<210> SEQ ID NO 2
<211> LENGTH: 81
<212> TYPE: PRT
<213> ORGANISM: Artificial sequence
<220> FEATURE:
<223> OTHER INFORMATION: Poly-CTL epitope construct

<400> SEQUENCE: 2

Met Leu Leu Ala Val Leu Tyr Cys Leu Glu Leu Ala Gly Ile Gly Ile
1               5                   10                  15

Leu Thr Val Tyr Met Asp Gly Thr Met Ser Gln Val Gly Ser Glu Val
            20                  25                  30

Asp Pro Ile Gly His Leu Tyr Phe Leu Trp Gly Pro Arg Ala Leu Val
        35                  40                  45

Glu Ala Asp Pro Thr Gly His Ser Tyr Gly Ser Gln Leu Ser Leu Leu
    50                  55                  60

Met Trp Ile Thr Gln Cys Phe Leu Ala Ser Asn Glu Asn Met Asp Ala
65                  70                  75                  80

Met
```